US009447442B2

(12) United States Patent
Whitton et al.

(10) Patent No.: US 9,447,442 B2
(45) Date of Patent: Sep. 20, 2016

(54) PRODUCTION OF BIOFUEL FROM TISSUE CULTURE SOURCES

(71) Applicant: Naturally Scientific Technologies Limited, Beaconsfield, Buckinghamshire (GB)

(72) Inventors: Peter Andrew Whitton, London (GB); Geoffrey Robert Dixon, London (GB); William Timothy Merrell, London (GB)

(73) Assignee: NATURALLY SCIENTIFIC TECHNOLOGIES LIMITED, Beaconsfield (GB)

( * ) Notice: Subject to any disclaimer, the term of this patent is extended or adjusted under 35 U.S.C. 154(b) by 0 days.

(21) Appl. No.: 14/100,197

(22) Filed: Dec. 9, 2013

(65) Prior Publication Data

US 2014/0199726 A1 Jul. 17, 2014

Related U.S. Application Data

(62) Division of application No. 12/989,733, filed as application No. PCT/GB2009/001066 on Apr. 28, 2009, now abandoned.

(30) Foreign Application Priority Data

Apr. 28, 2008 (GB) .................................. 0807619.2

(51) Int. Cl.
*C12P 7/64* (2006.01)
*C12N 9/18* (2006.01)
*C12N 9/20* (2006.01)

(52) U.S. Cl.
CPC ............... *C12P 7/6409* (2013.01); *C12N 9/18* (2013.01); *C12N 9/20* (2013.01); *C12P 7/649* (2013.01); *C12P 7/6463* (2013.01); *Y02E 50/13* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,936,139 A | 8/1999 | Schmid | |
| 5,965,755 A | 10/1999 | Semyk et al. | |
| 6,712,876 B2 | 3/2004 | Cao et al. | |
| 7,468,450 B2 | 12/2008 | Peter et al. | |
| 7,772,002 B1 | 8/2010 | Garces et al. | |
| 2002/0120957 A1 | 8/2002 | Duhot et al. | |
| 2002/0164797 A1 | 11/2002 | Martin et al. | |
| 2002/0197687 A1 | 12/2002 | Brunner et al. | |
| 2007/0028326 A1 | 2/2007 | Cirpus et al. | |
| 2007/0048848 A1 | 3/2007 | Sears | |

FOREIGN PATENT DOCUMENTS

| | | |
|---|---|---|
| CA | 2005462 | 6/1991 |
| DE | 3442145 | 5/1986 |
| DE | 100 59 372 | 6/2002 |
| EP | 1270734 | 1/2003 |
| GB | 1401681 | 7/1975 |
| JP | S57-074086 | 5/1982 |
| JP | 2010-063433 | 3/2010 |
| WO | WO 02/083888 | 10/2002 |
| WO | WO 2005/063999 | 7/2005 |
| WO | WO 2005/072529 | 8/2005 |
| WO | WO 2007/070452 | 6/2007 |
| WO | WO 2007/136762 | 11/2007 |
| WO | WO 2008/105618 | 9/2008 |
| WO | WO 2008/119082 | 10/2008 |
| WO | WO 2008/147781 | 12/2008 |
| WO | WO 2009/001315 | 12/2008 |
| WO | WO 2009/076559 | 6/2009 |
| WO | WO 2009/093367 | 7/2009 |
| WO | WO 2009/133351 | 11/2009 |

OTHER PUBLICATIONS

Weston and Street, "Sugar absorption and sucrose inversion by excised tomato roots", Ann Bot., 32: 521-529, 1968.
"Buffer Chart", available from http://medicine.ucsf.edu/labs/brown/protocols_03_2005/sigma_buffer_chart.pdf, Sigma Aldrich, 2000.
"Linsmaier and Skoog Medium", available from http://www.plantmedia.com/index.php?main_page=product_info&products_id=6740, Plant Media, downloaded Nov. 2014.
"Plant Cell Lines", available from https://www.dsmz.de/fileadmin/Bereiche/PlantCellLines/Dateien/LS.pdf, DSMZ GmbH, 2005.
"Product Catalog Results", available from http://www.caissonlabs.com/catalog.php?group=2&productline=6&family=54, Caisson Labs, downloaded Nov. 2014.
"Products", available from http://www.gendepot.com/kb/subview.php?sel_a=25&sel_b=26&sel_c=&idx=540&sel_page=sub_view_new, GenDepot, downloaded Nov. 2014.
"Technical Data", available from http://himedialabs.com/TD/PT040.pdf, HiMedia Labs, downloaded Nov. 2014.
Marziah, "Changes in pH of legume cell suspension culture media containing aluminum", *Developments in Plant and Soil Sciences*, 45:879-882, 1991.
"Ethanol Fuel," *Wikipedia, the Free Encyclopedia*, available online at www.wikipedia.com, accessed Mar. 13, 2009.
"Experimental Report Sent to EPO," Jun. 24, 2010.
"Linsmaier & Skoog Basal Medium pH adjusted and modified", Product information sheet, PhytoTechnology Laboratories, LLC. 2007.
"Linsmaier & Skoog Basal Medium", Product information sheet, PhytoTechnology Laboratories, LLC. 2007.
"Murashige and Skoog Salt Mixture (Powder)," *USBiological*, available online at http://www.usbio.net/item/M9503, accessed Feb. 21, 2011.
"Palisade cell", http://encyclopedia2.thefreedictionary.com/Palisade + cells, 2003.
Bambase et al., "Kinetics of hydroxide-catalyzed methanolysis of crude sunflower oil for the production of fuel-grade methyl esters," *Journal of Chemical Technology and Biotechnology*, 82: 273-280, 2007.

(Continued)

*Primary Examiner* — Paul Holland
(74) *Attorney, Agent, or Firm* — Parker Highlander PLLC

(57) ABSTRACT

A method for the production of at least one fatty acid and/or oil from a plant cell suspension culture includes (i) maintaining a cell suspension culture of oil-producing plant cells under conditions such that the cultured cells synthesize and secrete at least one fatty acid and/or oil into the cell suspension culture medium; and (ii) extracting the thus secreted at least one fatty acid and/or oil from the cell suspension culture medium.

32 Claims, 9 Drawing Sheets

(56) References Cited

OTHER PUBLICATIONS

Chapman et al., "N-acylethanolamines: formation and molecular composition of a new class of plant lipids," *Plant Physiol.*, 116:1163-1168, 1998.

Creelman et al., "Jasmonic acid distribution and action in plants: regulation during development and response to biotic and abiotic stress", *PNAS*, 92:4114-4119, 1995.

Delle Monache et al., "Comparisons between metabolite productions in cell culture and in whole plant of *Maciura pormifera*," *Phytochemistry*, 39(3):575-580, 1995.

Dong et at., "In situ carbon dioxide fixation in the process of natural astaxanthin production by a mixed culture of Haematococcus pluvialis and Phaffia rhodozyma ," *Catalysis Today*, 98(4):537-544, 2004.

English translation of International application No. PCT/JP2008/069523, filed Oct. 28, 2008 and published on Jul. 30, 2009 as International publication No. WO 2009/093367.

Gamborg and Shyluk, "The culture of plant cells with ammonium salts as the sole nitrogen source," *Plant Physiol.*, 45:598-600, 1970.

Hankamer et al., "Photosynthetic biomass and H2 production by green algae: from bioengineering to bioreactor scale-up", *Physiologia Plantarum*, 131:10-21, 2007.

Kim et al., "Effect of substrate concentration on hydrogen production and 16S rDNA-based analysis of the microbial community in a continuous fermenter", *Process Biochemistry*, 41:199-207, 2006.

Klinkenberg, Brian, Ed., "Introduction to plant taxonomy," *Electronic Atlas of the Plants of British Columbia (E-Flora BC)* Lab for Advanced Spatial Analysis, Department of Geography, University of British Columbia, Vancouver, available online at www.geog.ubc.ca/biodiversity/eflora/IntroductiontoPlantTaxonomy.html, 2010.

Leathers et al., "The effect of different temperatures on the growth, lipid content and fatty acid composition of Theobroma cacao cell suspension cultures," *Plant Science*, 62(2):217-227, 1989.

Martinez-Estevez et al., "Modification of the culture medium to produce aluminum toxicity in cell suspensions of coffee (*Coffea arabica* L.)," *Plant Cell Rep.*, 20:469-474, 2001.

May, "Transesterification of palm oil: effect of reaction parameters," *Journal of Oil Palm Research*, 16(2):1-11, 2004.

Murashige and Skoog, "Instructions for use: minimal organic powder medium," *SERVA ELCROPHORESIS*, Catalog No. 47515, Version May 2007, available online at http://www.serva.de/www_root/documents/47515_e.pdf, accessed Feb. 21, 2011.

Narváez et al., "Kinetics of palm oil methanolysism" *American Oil Chemists ' Society*, 84:971-977, 2007.

Office Communication issued in U.S. Appl. No. 12/989,733, mailed Nov. 19, 2012.

Office Communication issued in U.S. Appl. No. 12/989,733, mailed Jan. 28, 2013.

Office Communication issued in U.S. Appl. No. 12/989,733, mailed Jul. 12, 2013.

Office Communication issued in U.S. Appl. No. 12/989,733, mailed Sep. 18, 2013.

Office Communication issued in U.S. Appl. No. 12/989,733, mailed Nov. 19, 2013.

Parchmann et al., "Induction of 12-oxo-phytodienoic acid in wounded plants and elicited plant cell cultures," *Plant Physiology*, 115(3):1057-1064, 1997.

Paynich, "Transesterificatiort of vegetable oils to produce biodiesel fuel," *MMG 445 Basic Biotechnology eJournal*, 57-61, 2007.

PCT International Preliminary Report on Patentability, issued in International application No. PCT/GB2009/001066, dated Sep. 15, 2010.

Roitsch and Sinha, "Application of photoautotrophic suspension cultures in plant science," *Photosynthetica*, 40(4):481-492, 2002.

Schmidt et al.,"Metabolism of the environmental estrogen bisphenol A by plant cell suspension cultures," *Chemosphere*, 49(1).51-59, 2002.

Thorpe, "History of plant tissue culture", *Methods in Molecular Biology: Plant Cell Culture Protocols*, 318:9-32, 2006.

Westlake et al., "Triacylglycerol biosynthesis and gene expression in microspore-derived cell suspension cultures of oilseed rape," *Journal of Experimental Botany*, 49(318):33-39, 1998.

Whitton et al., "Kava lactones and the kava-kava controversy," *Phytochemistry*, 64:673-679, 2003.

Xu et al., "High quality biodiesel production from a microalga *Chlorella protothecoides* by heterotrophic growth in fermenters," *Journal of Biotechnology*, 126:499-507, 2006.

"Application Note", Denver Instrument, available from http://www.denverinstrument.com/denverusa/media/pdf/Reading_to_3-decimals_in_pH.pdf, accessed Feb. 2012.

"Hi 2216-0.001 Resolution pH/ORP/ISE/C Benchtop Meter", available from http://hannainst.com/usa/prods2.cfm?id=028001&ProdCode=HI%202216,.downloaded Jan. 2015.

"Orion™ PerpHecT™ 370 Benchtop pH/ISE Multiparameter Meter", Thermo Scientific Online Catalogue, accessed Feb. 2012.

Alberts et al., ed. *Molecular Biology of the Cell*. Garland Publishing: New York. $2^{nd}$ Ed. 1989. p. 1181.

Staswick and Tiryaki, "The oxylipin signal jasmonic acid is activated by an enzyme that conugates it to isoleucine in *Arabidopsis*", *The Plant Cell*, 16:2117-2127, 2004.

Yang et al., "Quantitiatvie profiling method for oxylipin metabolome by liquid chromatography electrospray ionization tandem mass spectrometry", *Anal Chem.*, 81(19): 8085-8093, 2009.

Fig. 5A

Table 1:

| GC oil method 4 | Sample No. | | | | | | |
|---|---|---|---|---|---|---|---|
| Compound | 1 % | 2 % | 3 % | 4 % | 5 % | 6 % | 7 % |
| 1-methoxy-3-(2-trimethylsilyloxyethyl)nonane | 2.24 | | | | | | |
| Adamantane-1-carboxamide, N-(2,4-dimethylphenyl)- | 8.91 | | | | | | |
| Butanoic acid, 2-[(trimethylsilyl)amino]-trimethylsilylester | 12.41 | | | | | | |
| Propanedioic acid, [(trimethylsilyl)-bis-(trimethylsilylester) | 15.17 | | | | | | |
| 3-methoxybenzylformic acid, trimethylsilylester | 13.65 | | | | | | |
| 4-methoxyandrost-4-ene-3, 17-diol, diacetate | 5.83 | | | | | | |
| pi.-cyclopentadienyl-dicarbonyl-ethylisonitril-trichlorgermyl-tungsten | 5.64 | | | | | | |
| Pentanoic acid, 2-[(tert-butyld... | 2.62 | | | | | | |
| Acetic acid, 2-[2,3-dihydro-4-(... | 4.15 | | | | | | |
| malonic acid, 2-(2,3 dihydroben... | 9.64 | | | | | | |
| benzamide, N-[1-(2,2-bis-tru... | 10.78 | | | | | | |
| 1, 4-cyclohexadiene, 1,3,6-tris(... | 3.44 | | | | | | |
| Pentadecanoic acid, 14-methyl, methyl ester (C15) | | | | 0.21 | 0.21 | | |
| Hexadecanoic acid, methyl ester (C16) | | | | 0.11 | 0.22 | 0.22 | |
| 9-octadecenoic acid (z)- methyl ester (C18) | | 76.52 | 78.17 | 84.59 | 77.07 | 73.59 | 61.93 |
| 9-octadecenoic acid methyl ester (C18) | | | | | 23.21 | | |
| 6-octadecenoic acid, methyl ester (C18) | | 14.16 | 6.74 | | | | |

Fig. 5B

| GC oil method 4 | Sample No. | | | | | | |
|---|---|---|---|---|---|---|---|
| Compound | 1 % | 2 % | 3 % | 4 % | 5 % | 6 % | 7 % |
| 11-octadecenoic acid methyl ester (C18) | | 5.82 | | | 6.8 | | |
| 8-octadecenoic acid, methyl ester (C18) | | | 13.09 | | 13.85 | | |
| 11-Eicosanoic acid, methyl ester (C20) | | | | 0.35 | | | |
| Eicosanoic acid, methyl ester (C20) | | 0.02 | 0.16 | 0.2 | | 0.22 | |
| Docasanoic acid, methyl ester (C22) | | 0.13 | 0.39 | 0.65 | | 0.21 | |
| 9, 12, 15-octadecatrien-1-ol (C18) | | | | 12.44 | | | |
| 1,5-Cyclooctadiene (EZ) (C8) | | | | | | | 35.14 |
| Total Methyl Esters | 0 | 96.65 | 98.55 | 98.55 | 97.94 | 97.45 | |
| Total Constituents | 94.48 | 96.65 | 98.55 | 98.55 | 97.94 | 97.45 | 97.07 |
| % Methyl Esters | 0 | 100 | 100 | 100 | 100 | 100 | |

Table 1. GC results of oil transesterification and Fenton reaction

PRODUCTION OF BIOFUEL FROM TISSUE CULTURE SOURCES

This application is a divisional of U.S. application Ser. No. 12/989,733, filed Oct. 26, 2010, as a national phase application under 35 U.S.C. §371 of International Patent Application No. PCT/GB2009/001066 filed Apr. 28, 2009 which claims priority to United Kingdom Patent Application No. 0807619.2 filed Apr. 28, 2008. The entire texts of the above-referenced disclosures are specifically incorporated herein by reference without disclaimer.

FIELD OF THE INVENTION

The invention relates to the production of vegetable oils, fatty acids and other biofuel sources from plant cells grown in tissue culture.

INTRODUCTION

The listing or discussion of an apparently prior-published document in this specification should not necessarily be taken as an acknowledgement that the document is part of the state of the art or is common general knowledge.

It is well known and reported that the use of fossil fuels is damaging to the environment and the atmosphere of the planet. Also it is well known that fossil fuels are a finite resource that cannot last indefinitely.

As a result of this there has been much research and investigation of alternative fuel sources such as nuclear, wind, solar, hydrogen fuel cells and biofuels.

The demand for biological derived fuel i.e. fatty acid methyl esters has grown exponentially recently due to various international governmental initiatives to reduce the reliance on petroleum derived fuel sources such as diesel oil and petrol (gasoline).

In order to meet this demand there has been increased pressure on agriculture to devote more land and resource to growing oil crops such as soybean, rapeseed and corn (maize) and so therefore there is less land available for the production of foodstuffs. This demand has also lead to deforestation of certain areas in order to plant oil seed crops.

It is obvious to those skilled in the art that this process is more likely to lead to increased global warming and third world poverty than to relieve it.

Plant cell tissue culture is known as a method of either propagating plants or for growing specific tissues of plants in order to harvest specific plant products.

It is also apparent that the production of vegetable oil for fuel production is extremely land intensive as less than one tonne of oil is produced per acre of land devoted to its production. This is due to the fact that only the seeds of the plant produce oil and only certain tissues within the seed. The rest of the plant tissue is therefore wasted in this method of production. Also each plant must be planted at a certain distance from its neighbour (this distance will be dependant on the plant species used).

Therefore it has become apparent that in order to satisfy increasing global demand for biofuels then an alternative source or method of producing these fuels is required.

The current process for the production of fatty acid methyl esters from the vegetable oils also has a major drawback as in the production of the methyl esters the triglyceride in the oil is decomposed into free fatty acids and glycerin. The volume of glycerin produced by this method is currently more than the demand from industrial sources for the product. This will then lead to further problems in the future as methods for the safe disposal of glycerin on a large scale will have to be developed.

It is well known in the art that plant cells may be maintained in tissue culture. Tissue culture is a term used to describe the process where plant cells are grown outside of an intact plant in a suitable nutrient medium. Tissue culture is defined as a method wherein parts of a plant are transferred into an artificial environment in which they can continue to survive. The term tissue culture as understood in the art refers to cultured tissue which may consist of individual or groups of plant cells, protoplasts or whole or parts of a plant organ.

In tissue culture, plant cells can be grown on a solid surface as pale coloured lumps known as callus culture or as individual or small clusters of cells known as suspension culture. Cells grown in culture are actively dividing and can be maintained in an indefinitely in an undifferentiated state by transferring the cells to fresh media (subculturing). Cultured cells may also be induced to redifferentiate into whole plants.

Tissue culture is well known in the field of plant biology and has several applications, for example it may be used to produce large quantities of plants or plant material in a short period of time (micropropagation).

Plant tissue cultures can be initiated from almost any part of the source plant (termed explant) although younger parts of the plant are generally more useful as they contain more actively dividing cells.

Although tissue culture is well known in the art different plants may vary in the exact conditions required to maintain the cells in culture.

Cells in tissue culture are generally different from those in an intact plant. It is also well known in the art that cultured plant cells produce different amounts and altered amounts of metabolites (Dicosmo and G Delle Monache, 1995, *Phytochemistry*, 39, 575-580).

The present inventor has surprisingly shown that cultured cells from the seed of *Triticum vulgare* and also from the soybean have surprising similar fatty acid and triglyceride profile to that of the compounds found in the whole plant or parts thereof other than isolated cells. The inventor has produced a culture of plant cells isolated from *Triticum vulgare* and has produced a stable plant cell line in culture.

As plant cells propagate within a few days it is inexpensive to produce large quantities of the cultured cell by subculturing. Therefore plant cell cultures of conventional vegetable oil bearing plant crops provide a convenient and inexpensive alternative to conventional agriculturally produced vegetable oil crops. Further more the addition of enzyme inhibitors (i.e. enzymes that act as inhibitors, such as lipase or esterase, as discussed further below) can prevent, reduce or reverse the addition of glycerine to the fatty acids and so remove the need for production of waste during the fatty acid extraction.

DESCRIPTION OF THE INVENTION

In accordance with a first aspect of the invention there are provided cultured plant cells, for example, of the genus *Triticum* (or other oil seed plant), characterized in their ability to produce both free fatty acids and plant lipids or oils.

The present invention will now be further described. In the following passages different aspects of the invention are further defined in more detail. Each aspect so defined may be combined with any other aspect or number of aspects unless clearly indicated to the contrary. In particular any feature indicated as being preferred or advantageous may be combined with any other feature or features indicated as being preferred or advantageous.

In the context of any of the following aspects of the invention, the term "plant" is preferably intended to exclude algae. Thus, any reference to a plant or plant cell may be construed to include the meaning that it is a non-algal organism or cell.

The cells of the invention are characterized in that they produce at least one fatty acid or oil compound which may be utilized as a fuel (or biofuel) or chemically modified in order to be utilized as a fuel (or biofuel). According to the invention the term produce is used to describe that plant cells make a compound that may then be retained within the cell, for example in the vacuole or in a storage organ, or which may be secreted.

The plant cells according to the invention have been isolated from their natural environment. A number of techniques for isolation of cells are known in the art. For example, the cells may be isolated by cutting a small piece of plant tissue. A skilled person will appreciate that any of the methods known in the art can be used according to the invention it will be understood by the skilled person that the invention can be carried out using cells isolated from different parts from one or more plants. For example, cells may be isolated from the mesoderm as exemplified in Example 1.

It will also be understood by a person skilled in the art that the total number of cells isolated may vary. In principle, there must be at least one cell as this cell will divide and multiple. However, starting from a single cell requires precise isolation of a single cell and is therefore time consuming. Accordingly, the total number of cells according to the invention may vary.

The terms cells 'in culture' or 'cultured cells' are used herein to refer to tissue culture of plant cells. Tissue culture refers to methods wherein plant cells derived from any part of the plant are grown in isolation from intact plants in nutrient media under controlled and sterile conditions. Nutrient media commonly used in the art comprise carbohydrate as a source of energy, salts, vitamins, amino acids, minerals, plant growth hormones and other compounds. The media may also comprise antibacterial and fungicidal compounds to prevent contamination by bacteria and/or fungi.

A number of different tissue culture methods are well known in the art and a skilled person will appreciate that the cells according to the invention may be cultured according to any of these methods. Such methods include, for example, tissue culture using Petri dishes and solid agar medium. Another well known culture method is suspension culture wherein the cells are suspended in a liquid and stored in flasks. Furthermore, plant cells may also be cultured using adherent plant cell cultures wherein cells are immobilized on gels, foams or membranes.

The cells are also characterized in that they are maintained and propagated in culture. Plant cell suspension cultures may be preferred.

Cultured plant cells according to the first aspect of the invention may be obtainable by isolating cells from a whole plant or parts of a plant and maintaining the cells in a culture medium. As described above, methods for isolating and culturing plant cells are well known in the art.

The skilled person will appreciate that cultured plant cells may secrete compounds into the surrounding medium. Accordingly, in one embodiment of the first aspect of the invention, the cultured cells of the invention secrete at least one compound which is a fatty acid and/or oil into the culture medium. If the cells according to the invention secrete the compound into the surrounding medium it is then possible to extract the fatty acid and/or oil fraction from the medium to use in the manufacture of biofuel.

As explained above, one way of tissue culturing plant cells is by suspension culture. In a suspension culture, small clusters of cells are grown in a flask suspended in a culture media. The culture or nutrient media typically comprise carbohydrates as a source of energy, salts, vitamins, amino acids, minerals, plant growth hormones and other compounds. The flasks or vessels containing the cells and the culture media are typically stored on a shaker, or contain a stirring mechanism, to prevent the cells from settling at the bottom of the flask or vessel. Suspension cultures are typically sub-cultured at specified intervals, for example about every one, two, three, four or five weeks (in this context "about" refers to ±4, 3, 2 or 1 days), to provide fresh growth media and to maintain the cells in a differentiated or undifferentiated state.

According to one embodiment of the first aspect of the invention, the media in which the cells are suspended and into which at least one compound comprising fatty acid and/or oil is secreted can be collected. The resulting liquid can be fractionated to remove the compound. Alternatively, the media may provide conditions that result in the passive separation of secreted fatty acid and/or oil from the media, to form a discrete layer that can be collected.

Accordingly, in a one embodiment of the first aspect, the present invention provides a method for the production of at least one fatty acid and/or oil from a plant cell suspension culture, the method comprising—

(i) maintaining a cell suspension culture of oil-producing plant cells under conditions such that the cultured cells synthesise and secrete at least one fatty acid and/or oil into the cell suspension culture medium; and (ii) extracting the thus secreted at least one fatty acid and/or oil from the cell suspension culture medium.

Plant cell suspension media of the art typically employ a pH of around neutral (i.e. about pH 7) when diluted to an operational concentration of its components. The present inventor has realised that such 'standard' culture pH conditions may not be optimal for the release of fatty acids and/or oils by plant cell suspension culture of the first aspect of the invention.

The plant cell suspension culture of the first aspect of the invention may be maintained at a pH suitable to cause fatty acids and/or oils stored in the vacuole of the cultured plant cells to be released, via the cytosol of the plant cells, into the cell suspension culture medium. Thus, the plant cell suspension culture may be maintained at a pH that is typically less than about pH 7.0, 6.5, 6.0, or more preferably 5.5, such as about, or greater than, pH 3.0 to about 6.5, preferably about, or greater than, pH 3.5 to about 5.5, more preferably about pH 4.5 to about 5.0 or 5.5. In this context, the term "about" may refer to ±0.5, 0.4, 0.3, 0.2, or 0.1 pH units. Plant cell cultures typically become non-viable below about pH 3.0, although the exact limit of this may vary between different plant cell suspension cultures depending, for example, on the species of plant or type of cell from which the cell culture is derived, and can be determined by routine testing on a culture-by-culture basis. In practice, the plant cell suspension culture should be maintained at a pH above the lower pH limit at which the cell culture in question becomes non-viable. In any case, most, if not all, plant cell suspension cultures should be viable and productive in the most preferred pH range of about pH 4.5 to about 5.5.

Thus, the cell suspension culture medium may comprise a buffer that maintains the cell suspension culture medium at around the selected pH. Any suitable buffer may be used. For example, the buffer may selected from the group consisting of citric acid and disodium hydrogen orthophosphate, or any other non-toxic buffer that contains no heavy metals and/or that is suitable for use in agriculture or food production.

The ionic strength of the cell suspension culture medium may, for example, be between 0.001M and 0.1M, preferably between 0.005 and 0.05M. In one embodiment, it is preferable to control the ionic strength of the cell suspension culture medium by the concentration of sugars, rather than the concentration of salts, because this allows for higher sugar concentrations, which can also be used as a carbon source by the cells in the culture. Typically the sugar or sugars used to control ionic strength are mono- or disaccharides, such as one or more of glucose, sucrose and/or fructose. The combined concentration of sugars within the culture medium may be about 30-70 g/L, 40-60 g/L or 50-60 g/L. About 50 g/L may be optimal. In this context, the term "about" refers to ±5, 4, 3, 2, 1 or 0.5 g/L.

The conductivity of the cell suspension culture medium may be maintained at a constant (for example, by limiting fluctuations in conductivity to no more than ±30%, 25%, 20%, 15%, 10%, 5%, 4%, 3%, 2%, 1% or substantially 0%). The optimal conductivity which will vary according to the species of plant used in the culture, and this can be determined by routine experimentation by the skilled person. Conductivity can be monitored and/or controlled by means well known in the art.

In a preferred embodiment, the viability of the plant cell suspension culture is maintained during the step of extracting the thus secreted at least one fatty acid and/or oil from the cell suspension culture medium. In other words, the step of extracting the thus-produced at least one fatty acid and/or oil does not require any, or any substantial, disruption of the growth of the plant cell suspension culture which may, for example, be adjudged by monitoring the level of respiratory activity as indicated by $O_2$ consumption and/or fatty acid and/or oil production, wherein the level of respiratory activity, and/or fatty acid and/or oil production, during the step of extracting the thus secreted at least one fatty acid and/or oil from the cell suspension culture medium should not drop to less than 50%, 60%, 70%, 80%, 90%, 95%, 99% or substantially 100% of the level observed when the extracting step is not being performed. Therefore, the present invention provides a method that allows for the continuous harvest of at least one fatty acid and/or oil from the cell suspension culture medium. This can be achieved by at least two approaches—

In a first approach to continuous harvest, the pH at which the cell suspension culture medium is maintained is selected to promote the secretion of fatty acids and/or oils from the cultured cells into the cell culture medium and further to promote the release of the secreted fatty acids and/or oils from an emulsion within the cell suspension culture medium, such as a an acidic pH of about, or above, 4.5, such as up to about pH 5.0, 5.5, 6.0, or 6.5. Without being bound by theory, the present inventor believes that, at this culture pH, the cytoplasm of the cultured plant cells becomes mildly acidified, which results in the release of fatty acids and/or oils from intracellular storage sites (such as the vacuole) into the cytoplasm as a micro-emulsion, followed by secretion/release of the fatty acids and/or oils into the cell culture medium, whereupon the chosen culture pH (along with other parameters, including ionic strength, temperature and pressure) cause the breakdown of the emulsion (if the culture pH is lower than about 4.5 then the emulsion may be maintained within the cell culture medium, for which see the second approach, below). As a consequence of the breakdown of the emulsion within the cell culture medium, the non-emulsified at least one fatty acid and/or oil is no longer miscible with the aqueous cell culture medium and, therefore, collects as a discrete layer on the surface of the cell culture medium. Thus, the secretion of the at least one fatty acid and/or oil from the cultured cells into the surrounding cell suspension culture medium may result in the formation of a biphasic system in which the at least one fatty acid and/or oil collects in a separate layer to the cell suspension culture medium. In such a biphasic system, the step of extracting the thus secreted at least one fatty acid and/or oil from the cell suspension culture medium may comprise direct extraction of the at least one fatty acid and/or oil from the layer that it forms within the biphasic system. It may be preferred to not completely remove of the layer, so that it can also continue to act as a barrier to pathogen movement between the atmosphere and the cell suspension culture medium.

In a second approach to continuous harvest, the pH at which the cell suspension culture medium is maintained is within the range of about, or greater than, 3.0 to about 4.5, preferably a pH within the range of about, or greater than, 3.5 to about 4.5, and this is selected to maintain the thus secreted fatty acids and/or oils in an emulsion within the cell suspension culture medium. In this approach, it is necessary to collect and process a part, or the whole of, the cell suspension culture medium to extract the at least one fatty acid and/or oil. Typically, this is done by physically separating a part or whole of the cell suspension culture medium from the cultured cells (optionally, done sequentially or simultaneously with the addition of fresh replacement culture medium) prior to processing, such as by filtration, dialysis, molecular filtration, or Vortex centrifugation. After processing the cell suspension culture medium to extract the at least one fatty acid and/or oil, the thus-processed cell suspension culture medium may be returned to the culture vessel to support the continued growth of the cultured cells. Typically, the step of processing the cell suspension culture medium to extract the at least one fatty acid and/or oil involves subjecting the cell suspension culture medium to a step that breaks the emulsion and thus allows the generation of a biphasic system, of the type described above, in which the at least one fatty acid and/or oil collects in a discrete layer separate to the cell suspension culture medium and can thus be collected. Therefore, where the thus secreted at least one fatty acid and/or oil is present in the cell suspension culture medium as an emulsion, it may be extracted from the cell suspension culture medium by processing the whole, or part, of the cell suspension culture medium to break the emulsion, optionally following the separation of the cell suspension culture medium from the cultured cells. The emulsion may be broken by any suitable means. For example, it may involve the step of processing the whole, or part, of the cell suspension culture medium—

(a) by modifying at least one condition of the cell suspension culture medium selected from the pH, ionic strength, temperature or pressure so that the at least one fatty acid and/or oil present therein is released from an emulsion; increases in temperature and/or reduction in pressure may be preferred since media treated in the manner can most conveniently be rendered suitable (e.g. by subsequent cooling and/or allowing a return to original pressure) for a return to the growing cell culture. Where pH and/or ionic strength is modified to break the emulsion, then typically the same condition(s) will be further modified prior to returning the medium to the growing cell culture to render it or them suitable for maintaining the culture conditions; and/or (b) by physically (mechanically) treating the cell suspension culture medium, such as by centrifugation, so that the at least one fatty acid and/or oil present therein is released.

Alternatively, the emulsion of the at least one fatty acid and/or oil may be extracted from the cell suspension culture medium by solvent extraction.

In a variant of the above discussed embodiments, the invention relates to cultured plant cells according to the invention characterized in that the cells are treated following culturing to remove the fatty acid and/or oil. In one embodiment the cells are lysed and then solvent extraction is performed to remove the fatty acid and/or oil. In another embodiment the cells are pressed to remove the fatty acid and/or oil. In yet a further embodiment the cells are homogenized. Homogenization may be used prior to washing the fatty acid and/or oil from the cells using water or another preferred solvent.

In this variant embodiment, in which cells of the culture are treated to remove the fatty acid and/or oil, such as by methods involving cell lysis, pressing or homogenization, then the process is a method that causes disruption of the growth of the plant cell suspension culture and, therefore, is a method for the non-continuous harvest of at least one fatty acid and/or oil from the cell suspension culture medium.

In a preferred embodiment the organic solvent comprises an alcohol. Preferably, the alcohol is a $C_1$ to $C_4$ alcohol. Preferably, the alcohol is a linear or alkyl alcohol. The alcohol may preferably be methanol, ethanol or propanol.

In another embodiment, the polar organic solvent comprises a haloalkane. Preferably the haloalkane is a $C_1$ to $C_4$ haloalkane. Also preferably, the haloalkane comprises chlorine. The chlorine may be present as $Cl_1$ to $Cl_4$. For example the haloalkane may be trichloromethane (chloroform), chloromethane or dichloromethane.

Another polar organic solvent that may be used is a carbonyl alkane. Preferably the carbonyl alkane comprises $C_1$ to $C_4$. In a preferred embodiment the carbonyl alkane is acetone.

It is also possible to use combinations of the polar organic solvents described above. For example, the solvent may comprise an alcohol and a haloalkane, an alcohol and a carbonyl alkane or a carbonyl alkane and a haloalkane. In a preferred embodiment, the solvent comprises a mixture of methanol and chloroform. In another preferred embodiment, the mixture of methanol and chloroform contains both compounds in equal parts.

In a preferred embodiment the above mentioned method of non-continuous harvest may include a step in which the plant cells may be dried in an oven or by other methods of removing water known to persons skilled in the art.

The oil-producing plant cell in the plant cell suspension culture of the first aspect of the present invention may be a differentiated plant cell, such as a cell that is specialised in the production and storage of oils, for example a mesoderm cell. The oil-producing plant cell may, although typically will not, be capable of photosynthesis to a level that removes the need for the culture medium in which it is grown to be supplemented by sugars, such as glucose, sucrose and/or fructose.

The oil-producing plant cell in the plant cell suspension culture of the first aspect of the present invention may be from an oil-producing plant, such as a plant selected from the group consisting of *Triticum, Brassica, Zea, Rhus, Olea* and *Glycine*.

The inventor has surprisingly shown that cells isolated from a plant from the genus *Triticum* and propagated in culture according to known methods in the art produce a very similar profile of fatty acid and oil compounds compared to the profile of fatty acid and oil compounds found in a whole *Triticum* plant. Accordingly the inventor is the first to show that vegetable oils can be produced from tissue cultured plants.

This is an unexpected and surprising result as it is well know in the art that plant cells which are maintained in culture produce different quantities of metabolites than in vivo cells. In some cases, metabolites present in the intact plant are absent in cultured cells (Delle Monache, 1995, *Phytochemistry*, 39, 575-580). To verify that the cells produce fatty acids and/or oils these fractions can be identified using conventional chemical techniques. A person skilled in the art will appreciate that such techniques include, but are not limited to, chromatographic methods and nuclear magnetic resonance. Therefore, the person skilled in the art will be able to identify the presence of fatty acids and/or oil compounds in the cultured cells of the invention using routine methods and knowledge available in the art.

According to one preferred embodiment of the first aspect of the invention, the plant cells used are of the genus *Triticum*. In another preferred embodiment the cells are from the genus *Zea*. In another preferred embodiment the cells are from the genus *Rhus*. In another preferred embodiment the cells are from the genus *Olea*. In another preferred embodiment the cells are from the genus *Brassica*. In another preferred embodiment the cells are from the genus *Glycine*. In another preferred embodiment the cells are from the genus of any other suitable oil producing plant.

The oil-producing plant cell may, or may not, be genetically modified, such as to incorporate one or more genetic modifications (e.g. transgenes) that increase the level, or modify the type, of fatty acid and/or oil that it produces. As further discussed below, this may include a genetic modification to increase endogenous levels of, or encode non-native, lipase or esterase enzymes (which may, or may not, be presented with a secretion leader sequence) to prevent, reduce or reverse the glyceration of fatty acids and thereby increase the level of free fatty acid production with a concomitant reduction in the production of oils.

As discussed above, the plant cell suspension culture medium used in the first aspect of the present invention (and/or any other plant cell cultures discussed in this application) may comprise one or more antibacterial and/or fungicidal compounds to prevent contamination by bacteria and/or fungi. Any antibacterial and/or fungicidal compounds known in the art may be used, so long as they do not substantially prevent the growth of the plant cell suspension culture. In one embodiment, one or more of the antibacterial and/or fungicidal compounds is a plant resin, such as a resins (for example, a root extract or latex) obtained from plants such as the genus groups *Piper* (for example, *Piper methysticum*) and *Populus* (for example *Populus candicans*). Exemplary antibacterial and/or fungicidal compounds are described in Whitton et al, 2003, *Phytochemistry*, 64, 673-679 and WO 2005/072529, the contents of both of which are incorporated herein by reference.

The at least one fatty acid and/or oil that is produced by and/or extracted from the method of the first aspect of the present invention may be further processed to convert it to a biofuel, or is optionally further purified and/or used in a downstream process such as by incorporation into a food product, cosmetic, lubricant or any other product that comprises fatty acids, vegetable oils, or compounds derived therefrom. Suitable methods for the purification and processing of fatty acids and oils are known to the skilled person. For example, numerous methods for the conversion of vegetable oil to biofuel such as fatty acid methyl esters (FAME) are well known in the art and may be employed to convert the resultant fatty acids or oils obtained by the method of the first aspect of the present invention. In particular, as discussed below, the present invention also provides a new method for the production of biofuels from fatty acids and mono-, di- and tri-glycerides, and this new method may be used to convert the fatty acids or oils obtained by the method of the first aspect of the present invention to biofuel.

An extracted and/or purified fatty acid or oil obtainable according to the first aspect of the present invention may be at least 50%, 60%, 70%, 80%, 90%, 95%, 96%, 97%, 98%, 99%, 99.5%, 99.8%, 99.9% or substantially 100% (by weight) composed of fatty acids and/or oils. Methods are known in the art, for example, gas chromatography or electrophoresis, for the assessment of percentage weight composition of fatty acids and/or oils.

A further embodiment of the first aspect of the present invention provides a cell suspension culture of oil-producing plant cells as defined above.

A further embodiment of the first aspect of the present invention provides a use of the cell suspension culture of oil-producing plant cells as defined above to produce at least one fatty acid and/or oil, wherein the at least one fatty acid and/or oil is secreted into the cell suspension culture medium, and preferably wherein the secretion results in the production of a biphasic system in which the secreted at least one fatty acid and/or oil collects in a separate layer from the cell suspension culture medium, as described above.

A further embodiment of the first aspect of the present invention provides a buffered plant cell suspension culture medium having an acidic pH of less than about pH 7.0, 6.5, 6.0 or 5.5, such as about, or greater than, pH 3.0 to about 6.5, preferably about, or greater than, pH 3.5 to about 5.5, more preferably about pH 4.5 to about 5.5, that is suitable for culturing a plant cell suspension culture by a method according to the first aspect of the present invention. The medium may also comprise antibacterial and fungicidal compounds to prevent contamination by bacteria and/or fungi. The medium may also comprise chemical or enzyme inhibitors (such as lipase or esterase, as discussed further below) that can prevent, reduce or reverse the addition of glycerine to the fatty acids and so remove the need for production of waste during the fatty acid extraction. The medium may comprise other components that are standard in plant cell culture media and, may, for example, be based on the widely available Murashige & Skoog medium. Plant cell suspension culture media commonly used in the art comprise carbohydrate as a source of energy, salts, vitamins, amino acids, minerals, plant growth hormones and other compounds, and any or all of these components may also be present in the buffered plant cell suspension culture medium of the present invention. The ionic strength of the cell suspension culture medium may, for example, be between 0.001M and 0.1M, preferably between 0.005 and 0.05M. In one embodiment, it is preferable to control the ionic strength of the medium by the concentration of sugars, rather than the concentration of salts, because this allows for higher sugar concentrations, which can also be used as a carbon source by the cells in the culture. Typically the sugar or sugars used to control ionic strength are mono- or di-saccharides, such as one or more of glucose, sucrose and/or fructose. The combined concentration of sugars within the culture medium may be about 30-70 g/L, 40-60 g/L or 50-60 g/L. About 50 g/L may be optimal. In this context, the term "about" refers to ±5, 4, 3, 2, 1 or 0.5 g/L. Consequently the level of salts (such as salts selected from one ore more, such as all, of ammonium nitrate, boric acid, calcium chloride anhydrous, cobalt chloride.$6H_2O$, cupric sulfate.$5H_2O$, $Na_e$-EDTA, ferrous sulfate.7H2O, magnesium sulphate, manganese sulfate.H2O, molybdic acid (sodium salt).$2H_2O$, potassium iodide, potassium nitrate, potassium phosphate monobasic, zinc sulfate.7H2O) may be kept at low or typical levels, such as at or below about 4.4 g/L in total, despite the attainment of relatively high ionic strength in the medium (in this context, the term "about" is used to refer to values that are ±50%, 40%, 30%, 20%, 10%, 5%, 2% or 1% of the base value). The buffered plant cell suspension culture medium may further comprise one or more antibacterial and/or fungicidal compounds as discussed above.

The buffered plant cell suspension culture medium of the invention may be used to maintain a cell suspension culture of oil-producing plant cells as defined by the first aspect of the present invention such that the cells synthesise and secrete at least one fatty acid and/or oil into the cell suspension culture medium.

In a further embodiment of the first aspect of the invention, there is also provided an extract of at least one fatty acid and/or oil obtainable by the method of the first aspect of the invention, or a product comprising the extract, such as a food product, cosmetic, or lubricant.

In a further embodiment of the first aspect of the invention, there is also provided a product that results from the processing of an extract of at least one fatty acid and/or oil obtainable by the method of the first aspect of the invention. A particularly preferred product is a biofuel, such as FAME, produced by the processing at least one fatty acid and/or oil obtainable by the method of the first aspect the invention. A biofuel produced from at least one fatty acid and/or oil obtainable by the method of the first aspect of the invention typically has a highly uniform distribution of fatty acid chain lengths that is not observed in biofuels produced from vegetable oil collected from whole plants. Without being bound by theory, the present inventor believes that this is due to the highly consistent conditions experienced by oil-producing cells within the cell suspension culture of the first aspect of the present invention, compared to the more variable environmental conditions experienced by whole plants, such as whole plants grown in fields. Thus, whereas convention biofuels, such as FAME, derived from conventionally-produced vegetable oil may contain a variable distribution of fatty acid chain lengths, such as about 5% or more outside of two standard deviations from the predominating fatty acid chain length, biofuel produced by the method of the first aspect of the present invention may have a distribution of fatty acid chain lengths in which no more than about 5%, such as no more than about 4%, about 3%, about 2%, about 1%, about 0.5% or substantially 0% are outside of two standard deviations from the predominating fatty acid chain length. In this context, the term "about" indicates ±0.5, 0.4, 0.3, 0.2 or 0.1%.

The distribution of fatty acid chain lengths in a biofuel can be assessed by techniques well known in the art, including techniques discussed below in the examples. A person skilled in the art will appreciate that such techniques include, but are not limited to, chromatographic methods and nuclear magnetic resonance. Therefore, the person skilled in the art will be able to identify the presence and distribution of fatty acids and/or oil compounds in biofuels of the invention using routine methods and knowledge available in the art.

In the foregoing method of the first aspect of the present invention, the oil-producing plant cell that is present in the plant cell suspension culture, such as a cell that is specialised in the production and storage of oils, for example a mesoderm cell, may possess a low, or even non-existent, photosynthetic ability. It therefore requires the supply of a carbohydrate feedstock (for example, as discussed above, sugars including glucose, sucrose and/or fructose) to act as an energy source and substrate for the synthesis of fatty acids and/or oils.

The present inventor has realised that it would be convenient and beneficial to take advantage of the ability of suspension cultures of photosynthetic plant cells to produce their own sugars from light, water and carbon dioxide ($CO_2$), via the photosynthetic process, such that sugars are produced to use as an energy source for the growth of the oil-producing plant cells and as a substrate for their production of fatty acids and/or oils. In fact, the inventor has realised that it would be possible to take advantage of the photosynthetic process, to use a suspension culture of photosynthetic plant cells to generate a sugar source for use by any process that utilises sugars, such as any culture of biological material. Moreover, the inventor has realised that this allows for the capture of $CO_2$ by the suspension culture of photosynthetic plant cells, such as $CO_2$ that is released as a by-product of other processes, so that it can be utilised to produce useful sugars and simultaneously reduce the level of $CO_2$ that is released by $CO_2$-emitting processes, such as processes for the generation of electricity that use carbon-based fuels, or microbiological processes (such as, for the production of bioethanol) that release $CO_2$.

Accordingly, a second aspect of the present invention provides a method for the production of a biological product, the method comprising—

(i) maintaining a first cell suspension culture of photosynthetic plant cells under conditions that allow the cultured cells to photosynthesis and thereby generate and release sugars, typically mono- and/or di-saccharides (for example glucose, sucrose, and/or fructose), into the surrounding culture medium; and (ii) maintaining a second cell culture in the presence of the sugar generated by the first cell suspension culture to allow growth of the second culture and the production of a biological product.

The biological product may be the cells of the second cell culture, e.g. it may be biomass. Alternatively, the biological product may be synthesised by the cells of the second cell culture. Biological products synthesised by the second cell culture include at least one fatty acid and/or oil, a proteinaceous product (including recombinantly-encoded proteinaceous products) and/or a metabolite, such as ethanol.

The conditions that allow the cells of the first cell suspension culture to photosynthesis typically includes the provision of light, water and carbon dioxide. Preferably full spectrum light is provided. Preferably excess carbon dioxide is provided, that is, the level of carbon dioxide is not limiting on the photosynthetic process. Water is provided by the aqueous environment of standard plant cell culture media.

In one embodiment of the second aspect of the present invention, the cells of the first cell suspension culture and the cells of the second cell culture are in fluid communication with each other. Thus, for example, they may be mixed together and cultured in the same medium and in the same vessel. Alternatively, the cells of the first cell suspension culture and the cells of the second cell culture may be held in separate culture vessels, but those separate culture vessels may be connected in fluid communication with each other, so that sugars produced by the first (photosynthetic) cell suspension culture can be used by the cells of the second cell culture. This may be achieved, for example, with a 2 tank system with a filer between the tanks to prevent cross contamination of the cell lines. In other words, the fluid communication between the cells of the first cell suspension culture and the cells of the second cell culture may allow the sugar released by the cells of the first cell suspension culture to be used as a carbon source by the cells of the second cell culture.

In another embodiment of the second aspect of the present invention, the cells of the first cell suspension culture and the cells of the second cell culture are each grown in separate culture vessels that are not in fluid communication with each other. In that case, the sugar released by the cells of the first cell suspension culture is collected and then fed to the cells of the second cell culture for use as a carbon source. Thus, the method of the second aspect of the present invention may comprise the step of extracting sugar from the culture medium of the first cell suspension culture and the further step of feeding the extracted sugar into the second cell culture. Sugar may be extracted from the culture medium of the first cell suspension culture by any suitable means, such as by dialysis, molecular filtration, crystallisation and the like. The extract may itself be the culture medium that has been used for the culture of the first cell suspension culture (and thus enriched in sugars from the photosynthetic activity of the cells of the first cell suspension culture) from which the cells of the first cell suspension culture have been removed (e.g. by filtration), wherein the extracted sugar-enriched media is used directly as the media for the second cell culture. After depletion of the sugars from extracted sugar-enriched media occurs, as a consequence of growing the cells of the second cell culture in it, the cells of the second cell culture may be removed from the sugar-depleted media (e.g. by filtration) and the thus-produced cell-free sugar-depleted media may be returned for use as the culture medium of the first cell suspension culture so it can be regenerated (i.e. enriched with sugars from the photosynthetic activity of the cells of the first cell suspension culture) again.

Sugar may be extracted from the culture medium of the first cell suspension culture by continuously removing sugar from the cell culture medium of the first cell culture. In other words, sugar may be removed from the cell culture medium of the first cell culture without any, or any substantial, disruption of the growth of the first cell culture which may, for example, be adjudged by monitoring the level of photosynthetic activity as indicated by $CO_2$ consumption and/or sugar production, wherein the level of photosynthetic activity during collection of the sugar should not drop to less than 50%, 60%, 70%, 80%, 90%, 95%, 99% or substantially 100% of the level observed before sugar collection. Suitable techniques that enable for continuous removal of sugar are known in the art and include, for example, dialysis of the culture medium.

In an embodiment of the second aspect of the present invention, the second cell culture is maintained in the presence of sugar generated by the first cell suspension culture at a sugar concentration in the range of 0.01M to 1.5M, preferably at the concentration of about 50 g/L.

Any cells may be cultured in the second cell culture of the second aspect of the present invention. Typically, the cells may be prokaryotic or eukaryotic, such as bacterial, fungal, plant, animal or human cells. In order to combine the first and second aspects of the present invention, it may be preferred that the second cell culture is a cell suspension culture of oil-producing plant cells, such as a culture that is described above in respect of the first aspect of the invention. Alternatively, the second aspect of the present invention may be used independently of the first aspect. Thus, for example, the second cell culture may be a culture of microorganisms, such as bacteria or fungi, including yeast. Exemplary yeast include *Saccharomyces* species. In one embodiment, the second cell culture may be a cell culture for making ethanol or other equivalent biofuel (e.g. another alcohol) and thus the cells in the cell culture may be a microorganism, such as yeast, that can convert sugar into the ethanol or other equivalent biofuel. Thus, the cells of the second cell culture may be microorganisms, such as yeast (for example, a *Saccharomyces* species), and the biological product may be an alcohol, such as ethanol.

Typically, such cultures may, themselves, produce $CO_2$ as a waste product, in which case the $CO_2$ produced by the second cell culture can be made available as a sole, or supplementary, source of $CO_2$ to the first cell suspension culture of photosynthetic plant cells. This circuit of $CO_2$ release and capture can aid in making such processes more carbon-neutral (i.e. reducing overall $CO_2$ output)

In one preferred embodiment, the second cell culture is a cell suspension culture of oil-producing plant cells (such as a differentiated plant cell, for example a differentiated plant cell that is specialised in the production and storage of oils, such as a mesoderm cell) and so the method of the second aspect of the invention may be a method for the production of at least one fatty acid and/or oil from a plant cell culture, the method comprising maintaining a second cell suspension culture of oil-producing plant cells in the presence of the sugar generated by the first cell suspension culture and under conditions such that the cultured oil-producing plant cells produce at least one fatty acid and/or oil. In a particularly preferred embodiment, the features of the first and second aspects of the present invention are combined.

The method of the second aspect of the invention may comprise the step of extracting the biological product from the second cell culture. The nature of the extraction step will depend on the nature of the biological product and can be readily determined by the skilled person. Where the biological product produced by the second cell culture is at least one fatty acid and/or oil produced by a plant cell culture, then it may be extracted from the second cell culture by any suitable technique, such as any of the continuous or non-continuous processes discussed above in respect of the first aspect of the present invention.

The method of the second aspect of the invention may also comprise the step of further purifying and/or processing (including chemically modifying) the thus-extracted biological product. The nature of the purification and/or processing steps will depend on the nature of the biological product and can be readily determined by the skilled person.

Where the biological product produced by the second cell culture is at least one fatty acid and/or oil produced by a plant cell culture, then the at least one fatty acid and/or oil that is extracted may then be further processed to convert it to a biofuel (such as FAME), or is optionally further purified and/or used in a downstream process such as by incorporation into a food product, cosmetic, or lubricant.

In one embodiment, the photosynthetic plant cells present in the first cell suspension culture of the method of the second aspect of the invention may, or may not, be differentiated photosynthetic plant cells. The differentiated plant cell may be a cell that is specialised for photosynthesis, such as a cell from the leaf or green tissue of a plant, including palisade, leaf mesoderm or petiole cells. Palisade cells may be particularly preferred.

Photosynthetic plant cells present in the first cell suspension culture of the method of the second aspect of the invention may possess one of more characteristics selected from—

(i) as a mean average over 100 randomly sampled cells from the first cell suspension culture, the photosynthetic plant cells contain at least 10, 15, 30, 40, 50 or more chloroplasts per cell;

(ii) a higher chlorophyll content (preferably 2-, 3-, 4-, 5-, 10-, 20-fold or more) than cells of a mesoderm cell suspension culture derived from the same plant species, for example as determined by a spectrophotometric assay which compares the absorbance of a test sample at a wavelength 594 nm (which indicates chlorophyll content) to the absorbance of the same sample at a wavelength of about 1500 nm (which indicates cell density) such that chlorophyll content can be represented by the ratio of $Abs_{594}:Abs_{1500}$;

(iii) the ability to produce at least 30, 40, 50 or more g/L of sugar (such as glucose, sucrose and/or fructose) when maintained in cell suspension culture for a week at 20-24° C., under atmospheric pressure, in the presence of excess carbon dioxide, and with exposure to full spectrum light, with intensity at 594 nm of $15.12_{\times 10}{}^{-3}$ Watts; and/or (iv) the ability to capture at least 50, 75, 100 mg or more of carbon, per 100 g dry weight cells, per hour, when maintained in cell suspension culture at 20-24° C., under atmospheric pressure, in the presence of excess carbon dioxide, and with exposure to full spectrum light, with intensity at 594 nm of $15.12_{\times 10}{}^{-3}$ Watts.

Photosynthetic plant cells present in the first cell suspension culture of the method of the second aspect of the invention may be isolated from a copper-tolerant plant, such as from *Agrostis tenuis*.

The first cell suspension culture of photosynthetic plant cells of the second aspect of the present invention may have a cell culture medium copper level of 0.001 to 0.1M.

In the method of the second aspect of the present invention, the first cell suspension culture of photosynthetic plant cells may be fed carbon dioxide from a carbon dioxide source selected from liquid carbon dioxide or gaseous carbon dioxide. The liquid or gaseous carbon dioxide source may, or may not, be obtained wholly or partly as a by-product of a carbon dioxide-producing process, such as a process of power generation that uses carbon fuels, or a process of biofuel (such as bioethanol or other alcohols) production by microorganisms (such as yeast) that releases carbon dioxide.

Thus, in one preferred embodiment of the second aspect of the present invention, at least the first cell suspension culture, and optionally also the second cell culture, is or are maintained at the site of the carbon dioxide-producing process, such as at the site of a power (e.g. electricity) generating facility, or at the site of a biofuel (such as bioethanol or other alcohol) generating facility, that generate carbon dioxide as a by-product.

Accordingly, the second aspect of the present invention also provides a two-culture system for producing a biological product (for example, as defined above), comprising a first plant cell suspension culture and a second cell culture, each as defined above in respect of the second aspect of the present invention. The two-culture system may further comprises a carbon dioxide-generating source, and wherein the thus-generated carbon dioxide is fed into the first plant cell suspension culture. The carbon dioxide-generating source and the second cell culture may be the same or different.

In a preferred embodiment, the two-culture system of the second aspect of the present invention is a system for producing at least one fatty acid and/or oil, comprising a first plant cell suspension culture as defined above in respect of the second aspect of the present invention and a second plant cell suspension culture of oil-producing plant cells as defined above in respect of the first and/or second aspect of the present invention.

The second aspect of the present invention also provides a carbon dioxide capture system comprising at least the first plant cell suspension culture as defined above in respect of the second aspect of the present invention, and optionally also the second cell culture as defined above in respect of the second aspect of the present invention. The carbon dioxide capture system may comprises a carbon dioxide-generating source, in which case the thus-generated carbon dioxide is fed into the first plant cell suspension culture. The carbon dioxide capture system may comprise a second plant cell suspension culture of oil-producing plant cells as defined above in respect of the first and/or second aspect of the present invention.

The second aspect of the present invention also provides for the use of the two-culture system, or of the carbon dioxide capture system, to capture carbon dioxide. Typically, the carbon dioxide that is captured is the by-product of a carbon dioxide-producing process, such as a process of power (e.g. electricity) generation that uses carbon fuels, or a process of biofuel (such as bioethanol or other alcohol) production by microorganisms (such as yeast) that releases carbon dioxide. This use may take place at the site of the carbon dioxide-producing process, such as at the site of a power (e.g. electricity) generating facility, or at the site of a biofuel (such as bioethanol or other alcohol) generating facility or other commercial, industrial or natural process, that generates carbon dioxide as a by-product.

Accordingly, the second aspect of the present invention also provides a carbon dioxide-producing power (e.g. electricity) generating facility comprising the two-culture system as defined above by the second aspect of the invention, or the carbon dioxide capture system as defined above by the second aspect of the invention. In one embodiment, the two-culture system or the carbon dioxide capture system may produce at least one fatty acid and/or oil from the captured carbon dioxide and, optionally, the thus produced at least one fatty acid and/or oil may be used directly, or indirectly (e.g. by first converting to biofuel) to supplement the fuel used by the power generating facility.

The second aspect of the present invention also provides a carbon dioxide-producing biofuel (such as bioethanol or other alcohol) generating facility comprising the two-culture system as defined above by the second aspect of the invention, or the carbon dioxide capture system as defined above by the second aspect of the invention. The sugars produced by the first cell suspension culture of photosynthetic plant cells present within the two-culture system or the carbon dioxide capture system may be used to supplement the growth of microorganisms (such as yeast) used in the production of biofuel by the biofuel generating facility The second aspect of the present invention also provides an extract of a biological product obtainable by the method of the second aspect of the present invention. Thus, the extract may be an extract of at least one fatty acid and/or oil. The second aspect of the present invention also provides a biofuel obtainable by the processing of the extract of the at least one fatty acid and/or oil.

The second aspect of the present invention also provides for the use of an extract of a biological product obtainable by the method of the second aspect of the present invention, or a biofuel obtainable by the processing of the extract, as a supplementary source of fuel for a carbon dioxide-producing process.

In the foregoing methods of the first aspect and/or second aspect of the present invention that involve the production of fatty acids and/or oils, the production of biofuels such as FAME, from oils (i.e. fatty acids conjugated to glycerine) requires a reaction that lyses the oil to produce the biofuel and a side-product of glycerol. When produced in large quantities, as would be required to generate a commercially-relevant amount of biofuel from vegetable oils, glycerol can be a harmful and problematic side-product. The present inventor has realised that it would be convenient and beneficial to modify the production of oils by plant cell cultures by using an enzyme inhibitor that can prevent, reduce or reverse the addition of glycerine to the fatty acids and so reduce or remove the need for production of waste during the fatty acid extraction. In fact, the inventor has realised that it would be possible to take advantage of this approach in any method of making fatty acids and oils in plant cell cultures.

Accordingly, in a third aspect of the present invention, the is provided a method for the production of at least one fatty acid from a plant cell culture, the method comprising maintaining a cell suspension culture of oil-producing plant cells in the presence of an inhibitor of fatty acid glyceration such that the cultured cells produce at least one fatty acid. Accordingly, the method may include the step of adding at least one inhibitor of fatty acid glyceration to a cell suspension culture of oil-producing plant cells. Alternatively, the method may involve using oil-producing plant cells that have been genetically modified, such as to incorporate one or more genetic modifications to increase endogenous levels of an enzyme, or encode a non-native enzyme, (which may, or may not, be presented with a secretion leader sequence to effect secretion of the enzyme from the plant cell), which enzyme is able to prevent, reduce or reverse the glyceration of fatty acids and thereby increase the level of free fatty acid production with a concomitant reduction in the production of oils.

Suitable inhibitors that are able to prevent, reduce or reverse the glyceration of fatty acids may be enzymatic or a chemical inhibitors of glyceration. Enzymatic inhibitors include lipase and esterase enzymes. Wheatgerm or rapeseed lipase may be preferred. For example, wheatgerm lipase is available from Sigma Aldrich.

Suitable lipases (or lipase-coding DNA sequences) may also be obtained from microorganisms such as *Candida antartica, Rhizopus oryzae, Mucor miehei* and/or *Pseudomonas cepacia*.

There are many commercially available lipases that may be used. For example a suitable lipase maybe selected from the following list of commercially available lipases—lipase from *Aspergillus niger* (Sigma product code: 62301), *Aspergillus oryzae* (Sigma product code: 62285), *Aspergillus* sp. (Sigma product code: 84205), *Burkholderia* sp. (Sigma product code: 75577), *Candida antarctica* (Sigma product code: 65986), *Candida cylindracea* (Sigma product code: 62302 or 62316), *Candida lipolytica* (Sigma product code: 62303), *Candida rugosa* (Sigma product code: L1754, 90860 or L8525), *Chromobacterium viscosum* (Sigma product code: L0763), human pancreas (Sigma product code: L9780), *Mucor javanicus* (Sigma product code: L8906), *Mucor miehei* (Sigma product code: L9031 or 62298),

*Penicillium camemberti* (Sigma product code: 96888), *Penicillium roqueforti* (Sigma product code: 62308), porcine pancreas (Sigma product code: L0382, L3126, 62313 or 62300), *Pseudomonas cepacia* (Sigma product code: 62309), *Pseudomonas fluorescens* (Sigma product code: 28602 or 95608), *Pseudomonas* sp. (Sigma product code: L9518), *Rhizomucor miehei* (Sigma product code: L4277), *Rhizopus arrhizus* (Sigma product code: 62305), *Rhizopus niveus* (Sigma product code: 62310), *Rhizopus* oryzae (Sigma product code: 80612), *Thermomyces lanuginosus* (Sigma product code: L0777), *Thermus flavus* (Sigma product code: L3294), *Thermus thermophilus* (Sigma product code: L3419), or wheat germ (Sigma product code: L3001).

Paynich, 2007, Microbiol & Mol. Gen., 445, 57-61, discusses the use of lipases in chemical processes for the production of biofuel from vegetable oils, in which it is employed instead of a base catalyst such as sodium hydroxide to separate oils into fatty acids and glycerol. However, Paynich warns of the inhibitory effect of the released glycerol on lipase activity, due to competitive inhibition. In the third aspect of the present invention, this inhibitory effect is mitigated by using the lipase (or other inhibitor of fatty acid glyceration) in an 'in culture' system, rather than in a chemical process.

Where an enzymatic inhibitor is used, then the cell culture pH may be chosen to optimise the activity of the inhibitor. For example, lipase is typically more active at around pH 7. Accordingly, it may be beneficial to select a culture pH that is as close as possible to the enzyme's optimal pH. Of course, this may result in a compromise between the best pH for the enzymatic inhibitor activity and the best pH for secretion and collection of fatty acids and oils from the plant cell suspension culture as discussed above in respect of the first aspect of the present invention. The skilled person will be able to determine the optimal compromise between these competing aspects of the invention depending on the key objective of the process.

The third aspect of the invention may employ a level of inhibitor that is capable of reducing the level of glycerated fatty acids by up to, or at least, 1%, 2%, 3%, 4%, 5%, 6%, 7%, 8%, 9%, 10%, 20%, 30%, 40%, 50%, 60%, 70%, 80%, 90% or more, compared to the same culture system in the absence of the inhibitor. For example, the present inventor has found that, when 1 g of the wheat germ lipase was added to 100 ml of the suspension culture, the resulting oil showed a breakdown with 8% of the oil being non-glycerated fatty acids when compared to the normal cell suspension product. Higher levels of lipase activity would be expected to result in more than 8% non-glycerated fatty acids.

The third aspect of the present invention may be combined with either or both of the first or second aspects of the present invention for the production of at least one fatty acid and/or oil, by maintaining a cell suspension culture of oil-producing plant cells as defined in the first or second aspects of the present invention in the presence of an inhibitor of fatty acid glyceration such that the cultured cells produce at least one fatty acid and, more specifically, a greater level of non-glycerated fatty acids when compared to the same culture system in the absence of the inhibitor.

The method of the third aspect of the present invention may further comprising the step of extracting the at least one fatty acid. Accordingly, the third aspect of the present invention also provides a fatty acid extract obtainable by third aspect of the present invention. The extracted at least one fatty acid can, for example, be processed to produce a biofuel and, as such the third aspect of the present invention also provides a biofuel obtainable by that process.

The third aspect of the present invention also provides a cell suspension culture of oil-producing plant cells comprising an inhibitor of fatty acid glyceration as defined above. The third aspect of the present invention also provides for the use of the cell suspension culture to produce at least one fatty acid. In one embodiment of this use, at least one fatty acid and/or oil is secreted into the cell suspension culture medium, for example, in accordance with the methods of the first aspect of the present invention.

The third aspect of the present invention also provides a plant cell suspension culture medium comprising an inhibitor of fatty acid glyceration. The plant cell suspension culture medium may be one as defined above in respect of the first aspect of the present invention.

As discussed above, fatty acids and/or oils (such as those produced by the first, second or third aspects of the present invention) can be converted to biofuels, such as FAME.

Suitable methods for achieving this conversion are well known in the art and any can be applied to the treatment and processing of fatty acids and/or oils produced by the first, second and/or third aspects of the present invention. For example, Paynich, 2007, *Microbiol & Mol. Gen.*, 445, 57-61 reviews various methods for the transesterification of vegetable oils to produce biodiesel.

As discussed in Paynich (supra), art-known methods for the transesterification of vegetable oils to produce biodiesel typically involving reacting vegetable oils with methanol in the presence of an alkaline catalyst such as sodium hydroxide. As discussed in Paynich, at page 58, $1^{st}$ col., lines 9-12, these methods use a large excess volume of methanol compared to the amount of vegetable oil used, typically in a ratio of 6:1 of methanol to oil which are said to be need to drive the reaction to completion. With this ratio, Paynich reports, on page 58, col. 1, that a 96.8% yield of biodiesel was obtained from safflower. Likewise, Bambase et al, 2007, *J. Chem. Technol. & Biotechnol.*, 82, 273-280 reports, in the abstract, that methyl esters from crude sunflower oil were produced by methonolysis using a sodium hydroxide catalyst with methanol:oil ratios of 6:1-20:1. Navaraez et al, 2007, *J. Am. Oil Chemists' Soc.*, 84, 971-977 reports on a method of palm oil methanolysis and uses a methanol molar ratio of 6:1. May, 2004, *J. Oil Palm Res.*, 16, 1-11 teaches a methanol-to-oil molar ratio of 10:1. U.S. Pat. No. 6,712, 876 teaches preferred molar ratios of methanol to fatty acid triglyceride of 15:1 to 30:1. All of the foregoing methods can be used to produce biofuels from fatty acids and/or oils produced by the first, second and/or third aspects of the present invention.

However, the present inventor has recognised that the prior art methods of producing fuel rely on a large excess of methanol, which is can be costly and also result in a high level of methanol contamination of the thus produced biofuel (e.g. FAME), such as potentially a 50-60% (v/v), or higher, level of methanol to biofuel in the resultant biofuel product.

The present inventor has surprising found that it is possible to achieve efficient conversion of fatty acids and/or oils to biofuel by using much lower amounts of methanol. Specifically, the present inventor has shown that it is possible to obtain a yield of 93.4% using a methanol to oil ratio of about 1:7.5. In comparison to the prior art methods discussed above, this is a significant decrease in the amount of methanol used, with only a minor reduction in yield. For example, compared to the discussion in Paynich (supra) of a 96.8% yield of biodiesel from safflower when using a methanol:oil ratio of 6:1, the present inventor has achieved a process that uses approximately 45-fold less methanol, but only shows a yield drop of about 3.4%. This can significantly reduce the methanol-based costs of the biofuel conversion process. Moreover, the levels of methanol contamination of the thus produced biofuel (e.g. FAME) can be substantially reduced such as to less than 20%, 15%, 10%, 5% (v/v) or less.

Accordingly, in a forth aspect of the present invention, there is provided a method for producing biofuels from at least one fatty acid and/or mono-, di- and/or tri-glycerides comprising reacting—
   a first volume of the at least one fatty acid and/or mono-, di- and/or tri-glycerides with
   a second volume of a reactant selected from an alcohol, alkane or alkene,
   in the presence of a base catalyst, thereby to form the biofuel,
wherein the ratio of first volume to second volume is greater than 1:6, such as at least 1:5, 1:4, 1:3, 1:2, or 1:1. For example, the first volume of the at least one fatty acid and/or mono-, di- and/or tri-glycerides may be greater than the second volume of the reactant, that is, more than 1:1, such between 1:1 to 10:1, for example, at least 2:1, 3:1, 4:1, 5:1, 6:1 or 7:1, optionally less than 9:1 or 8:1, most preferably about 7.5:1.

The biofuel produced by the method of the fourth aspect of the invention may be a fatty acid methyl ester (FAME).

The at least one fatty acid and/or mono-, di- and/or tri-glycerides may comprise fatty acid units with a chain length of C8-C30. In one embodiment, the distribution of fatty acid chain lengths is no more than about 5%, such as no more than about 4%, about 3%, about 2%, about 1%, about 0.5% or substantially 0% outside of two standard deviations from the predominating fatty acid chain length. The fatty acid and/or mono-, di- and/or tri-glycerides may be at least one fatty acid or oil as produced by a cell suspension culture of oil-producing plant cells, such as those defined by any one of the first, second or third aspects of the present invention.

The reactant used by the method of the fourth aspect of the invention may be selected from a C1-C8 alcohol, C1-C8 alkane or C1-C8 alkene. In one embodiment, it is methanol.

The base catalyst used by the method of the fourth aspect of the invention may be selected from a Group I metal hydroxide, such as LiOH, NaOH, KOH. NaOH may be preferred. Suitable levels of base catalyst can be determined by routine techniques, but may, for example, be in the range of 0.1% w/v to 10% w/v, preferably at a mass to volume percentage of 0.5% to 2% w/v.

The method of the fourth aspect of the invention may comprise the following steps—
(i) mixing the first volume of the at least one fatty acid and/or mono-, di- and/or tri-glycerides and the second volume of a reactant selected from an alcohol, alkane or alkene, in the presence of the base catalyst for a period of time selected from 1-72 hours (preferably 6-48 hours, such as about 6, 12, 24 or 48 hours) at a temperature selected from 50-150° C. (preferably 60-100° C., such as about 65° C.);
(ii) reducing the temperature of the reaction mixture (for example to about room temperature, i.e. 15-30° C., such as about 20° C.) and continuing to mix at the reduced temperature for a period of time selected from 12-48 hours (preferably 16-24 hours, such as about 6, 12, 24 or 48 hours);
(iii) allowing the reaction mixture to settle such that a glycerine layer separates from a biofuel layer (for example, by allowing the reaction mixture to rest at about room temperature for about 1 hour; or by centrifugation); and
(iv) separating the glycerine and biofuel layers to obtain a biofuel extract; and
(v) optionally, treating the biofuel extract obtained from step (iv) to reduce the chain length of the fatty acid units, preferably to increase the level of octane, for example by treatment with hydrogen peroxide+iron (III) chloride or equivalent reagents, or by thermal or thermal acid cracking using techniques known in the art.

The method of the fourth aspect of the invention may provide a yield of biofuel that is greater than 50%, such as greater than 60%, 70%, 80%, 90%, 91%, 92% or 93%, preferably in the range of 93-94%.

The biofuel produced by the method of the fourth aspect of the invention may have a methanol content of less than 50% (v/v), such as less than 40%, 30%, 20%, or 10% (v/v).

The biofuel produced by the method of the fourth aspect of the invention may have a distribution of fatty acid chain lengths in which no more than about 5%, such as no more than about 4%, about 3%, about 2%, about 1%, about 0.5% or substantially 0% are outside of two standard deviations from the predominating fatty acid chain length.

The fourth aspect of the present invention also provides a biofuel obtainable by the method of the fourth aspect. Accordingly, the biofuel thus obtained may, for example, possess—
   (a) a methanol content of less than 50% (v/v), such as less than 40%, 30%, 20%, or 10% (v/v); and/or
   (b) a distribution of fatty acid chain lengths in which no more than about 5%, such as no more than about 4%, about 3%, about 2%, about 1%, about 0.5% or substantially 0% are outside of two standard deviations from the predominating fatty acid chain length.

BRIEF DESCRIPTION OF THE DRAWINGS

FIGS. 5A-5B show Table 1, as discussed in Example 2 below.

The invention will be further understood with reference to the following non limiting experimental examples.

EXAMPLE 1

FIG. 1-4 show a schematic diagram of an extraction process.

Figure 1:
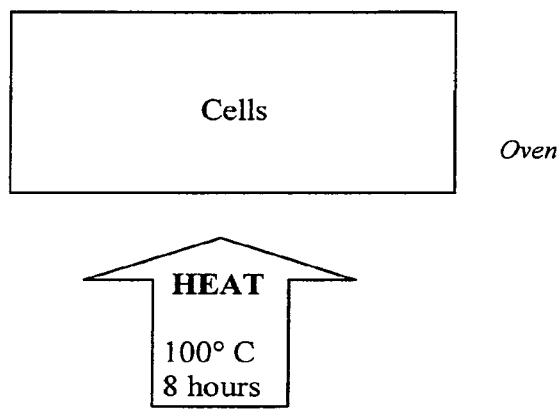
FIG. 1 is a schematic diagram of Stage 1 of an extraction process as described in Example 1, and shows the heat Treatment of Cells

1.1 FIG. 1 shows the heat treatment of freeze-dried cells, which represents Stage 1, in which cells of *T. vulgare* cell suspension culture PAW-NS-1 were heated for 8 hours in an oven set to 100° C.

Figure 2:
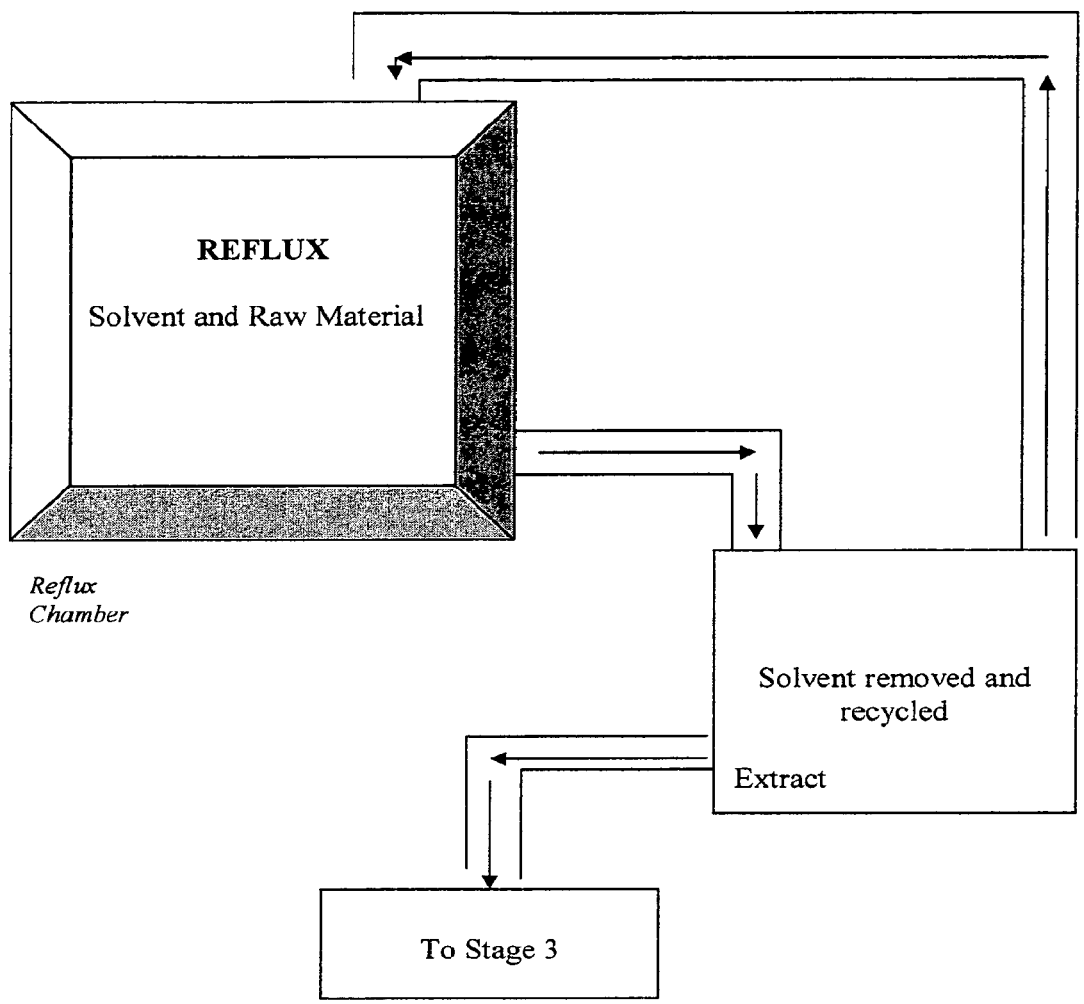
FIG. 2 is a schematic diagram of Stage 2 of an extraction process as described in Example 1, and shows the solvent extraction of cells

1.2 FIG. 2 shows the stage 2 of an extraction process for the solvent extraction of heat-treated cells. In Stage 2:
a) Heat treated cells are refluxed for one hour in a 1:1 mixture of chloroform and methanol.
b) Cell: solvent mixture is filtered.
c) Solvent is removed by rotary evaporation. Residue containing crude active extract is re-dissolved in chloroform and proceeds to Stage 3.
d) Used solvent is distilled and cycled back to reflux chamber for re-use.
e) Used cells are disposed of.

Figure 3:
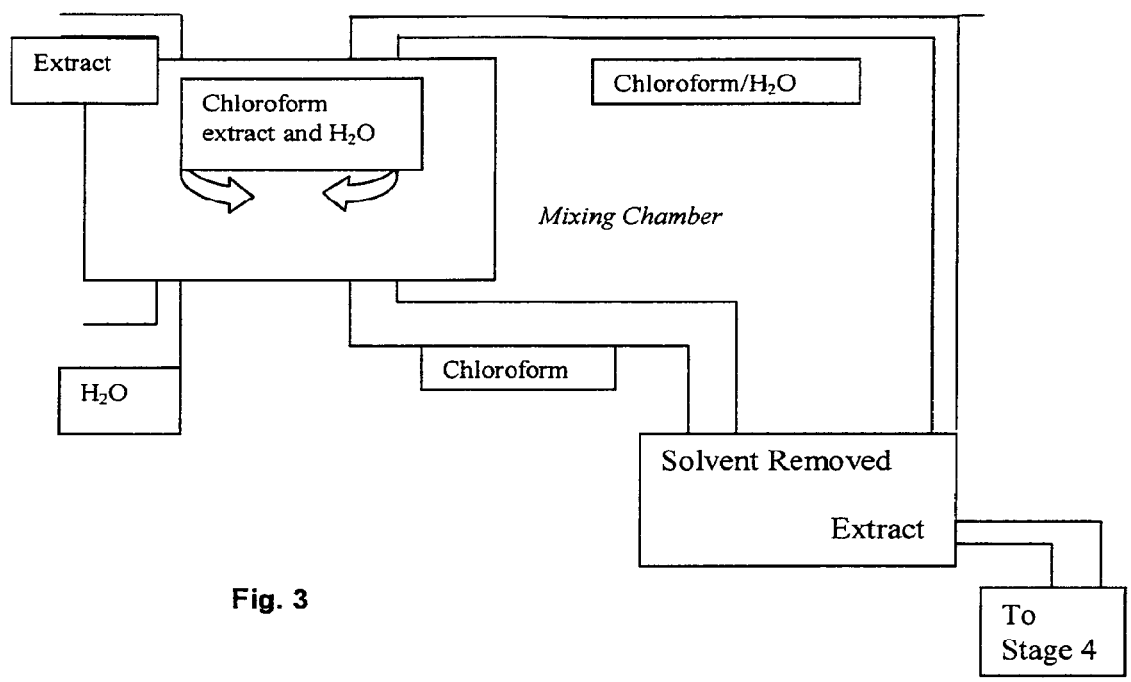
FIG. 3 is a schematic diagram of Stage 3 of an extraction process as described in Example 1, and shows the solvent extraction of cells

1.3 FIG. 3 shows the stage 3 of an extraction process for the solvent extraction of heat-treated cells. In Stage 3:
a) Crude active residue in chloroform is mixed with an equal volume of distilled water and mixed.
b) Phases are allowed to separate, and a metered tap is used to remove chloroform to a chamber.
c) Solvent is removed by rotary evaporation. Residue containing crude active extract is re-dissolved in methanol and proceeds to Stage 4.
d) Used solvent is distilled and cycled back to mixing chamber for re-use.
e) Water is disposed of.

Figure 4:
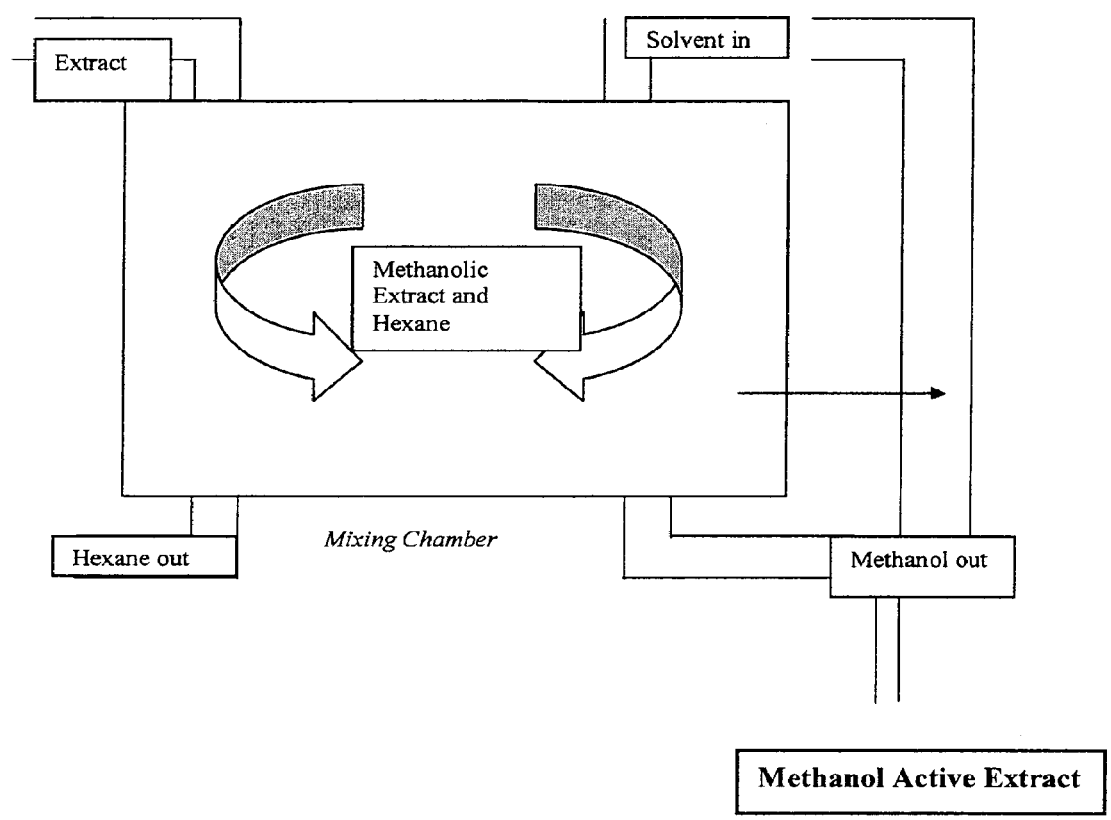
FIG. 4 is a schematic diagram of Stage 4 of an extraction process as described in Example 1, and shows the solvent extraction of cells

1.4 FIG. 4 shows the stage 4 of an extraction process for the solvent extraction of heat-treated cells. In Stage 4:
a) Crude active residue in methanol is mixed with an equal volume of hexane and mixed.
b) Phases are allowed to separate, and a metered tap is used to remove methanol to a chamber.
c) Solvent is removed by rotary evaporation. Residue containing pure active extract is obtained.
d) Used solvent is distilled and cycled back to mixing chamber for re-use.
e) Used hexane is distilled and reused.

5.0 Induction and Maintenance of *Triticum* Cell Suspension Culture
5.1 Initiation of callus cultures from *Triticum*—preparation of media
5.2 Initiation of callus cultures from *Triticum*—sterilisation of plant tissue
5.3 Media preparation
5.4 Inoculation and subculture 5.1 Initiation of Callus Cultures from *Triticum*: Preparation of Callus Induction Media
Callus Induction Media Solution;
Distilled $H_2O$ to 100%; 3.0% sucrose; 1.0% NAA (naphthalene acetic acid) 0.004% stock solution; 0.44% Murashige and Skoog Basal powdered medium
Equipment:
Glass bottle with cap; Magnetic stirrer; Sterile plastic plant culture dishes; Glass pipettes; pH meter; Autoclave; Laminar flow cabinet; Balance; Nescofilm; Phytagel; 1M NaOH solution; 0.1M NaOH solution.
a) Callus induction media was prepared using Murashige and Skoog (MS) media obtained from Sigma, with 3% sucrose and 1% naphthalene acetic acid (from a concentrated stock solution of 0.004% w/v.
b) The prepared media was pH was adjusted to pH 5.75 and solidified with 0.2% phytagel.
c) The media was autoclaved for 20 mins at 121° C. and then poured out into sterile plastic plant tissue culture dishes.

5.2 Initiation of Callus Cultures from *Triticum*: Sterilisation of Plant Tissue
Reagents:
Media prepared previously (section 5.1); *Triticum vulgare* plant tissue
Equipment:
Sterile glass beakers; Sterile distilled water; Sterile scalpel; Sterile tweezers; 10% bleach solution; 70% ethanol solution; 1M NaOH solution; 0.1M NaOH solution.
a) Plant tissue of *Triticum* was sterilised by immersion in 70% ethanol for 2 minutes, followed by immersion in 10% bleach solution for 10 minutes.
b) *Triticum* was then washed three times with sterile (autoclaved) distilled water.
c) The sterile *Triticum* was aseptically cut into disk shapes in a sterile laminar flow cabinet.
d) *Triticum* slices were placed onto the prepared plates containing callus induction media, and plates were sealed with Nescofilm.
e) The plates were placed in the dark at 27° C. and callus formation began to appear after about 1 month.

5.3 Media Preparation for Established Cultures
Reagents:
Distilled $H_2O$ to 100%; 3% sucrose; 0.44% Murashige and Skoog Basal powdered medium; 1% NAA (naphthalene acetic acid) 0.004% stock solution; 0.01% Vitamin solution (0.05% pyridoxalhydrochlorid, 0.10% thiamine dichloride and 0.05% g nicotinic acid); 1M NaOH solution; 0.1M NaOH solution.
Equipment:
1 L glass bottle: Magnetic stirrer; 20 250 m conical flasks; 20 sheets of foil approximately 20×20 cm; Glass pipettes; pH meter; Autoclave; Laminar flow cabinet; Balance.
Method:
a) Mix 3% sucrose, 0.44% MS powder, 1% NAA stock and 0.01% vitamin stock and prepare to 100% with distilled $H_2O$.
b) Mix using a magnetic stirrer until all dry components dissolved, then pH adjust with 1M and 0.1M NaOH, to 5.75.
c) Take 20 250 ml conical flasks. To each add 50 ml media and seal neck of flask with foil. Sterilize in autoclave, at 121° C., 103 kPa, for 25 minutes.
d) Immediately following sterilization, place flasks in laminar flow cabinet and allow to cool to ambient temperature.

5.4 Inoculation and Subculture of Established Cultures
Reagents:
Friable callus; 70% Ethanol.
Equipment:
Laminar flow cabinet; Bunsen burner; Prepared media; 20 sterile sheets of foil approximately 20×20 cm; Several pairs of tweezers or small forceps; Wide spatulas with holes.
Method:
a) Sterilize inside of laminar flow cabinet with 70% ethanol.
b) Sterilize all tweezers and spatulas by dipping in 70% ethanol, then flaming till red hot. Allow to cool inside laminar flow cabinet.
Initial inoculation:
a) Remove foil from prepared media flask.
b) Take sterilized tweezers and remove thumbnail sized pieces of friable callus from the plant tissue. Break up into finely dispersed cells and add to flask. Aim to add approximately 5 g tissue to 50 ml media (10% w/v)

c) Flame the neck of the flask, and cover with a sterile sheet of foil.

d) Place the flask on a shaker at 120 rpm, in a dark room heated to 27° C. Leave until a thick, dispersed cell suspension culture can be observed (approximately 2 weeks).

Subculture:

a) Remove foil from prepared media flask.

b) Remove foil from flask containing dispersed cell suspension cultures (produced by initial inoculation, point 6)

c) Take wide spatula with holes, sterilize, allow to cool and scoop out the cells. Add these cells to the fresh media. Aim to add approximately 5 g tissue to 50 ml media.

d) Flame the neck of the flask, and cover with a sterile sheet of foil.

e) Place the flask on a shaker at 120 rpm, in a dark room heated to 27° C. After 14 days, use the cell suspension culture for further subcultures.

6.0 Cell Suspension Culture 6.1 Media Preparation for Cell Suspension Cultures

Reagents:

Distilled $H_2O$ to 100%; 3% sucrose; 0.44% Murashige and Skoog Basal powdered medium; 1% NAA (naphthalene acetic acid) 0.004% stock solution; 0.01% Vitamin solution (0.05% pyridoxalhydrochlorid, 0.10% thiamine dichloride and 0.05% nicotinic acid); 1M NaOH solution; 0.1M NaOH solution.

Method:

a) Mix 3% sucrose, 0.44% MS powder, 1% NAA stock and 0.01% vitamin stock and prepare to 100% with distilled $H_2O$.

b) Mix until all dry components have dissolved, then pH adjust with 1M and 0.1M NaOH, to 5.75.

c) Sterilize media and allow to cool to ambient temperature before use.

6.2 Subculture Of Cell Suspension Cultures

Reagents:

Friable cells; Media prepared previously (section 5.1)

Method:

a) Take cell suspension culture in the exponential phase of growth.

b) Filter cells from media, and use these cells to inoculate fresh media. Aim to add cells to media at approximately 10% w/v.

c) Agitate the culture vessel at 120 rpm, at 27° C., and in dark conditions.

d) For further subcultures, the cells should be used when the culture has reached the logarithmic growth phase.

e) For harvesting of active compound, the cells should be used when the culture has reached the stationary phase.

EXAMPLE 2

This example provides a report on production of biofuel from vegetable oil. The method employed was as follows—

Production of Biofuel

Stage 1:

Vegetable oil was mixed with a 1.04M solution of sodium hydroxide (NaOH) in methanol (MeOH), in the ratio 187 mls oil to 25 mls NaOH/MeOH solution. This was mixed at 65° C. for 6 hours, and left mixing overnight (16 hours) at room temperature, 20° C. After this time, the mixture was left to settle for 1 hour at room temperature, after which time 2 layers had formed. The lower (glycerine) layer was removed using a separating funnel and the top layer was retained for further analysis and treatment.

Stage 2:

The Fenton reaction was induced in the top layer. This stage was performed in the fume hood, wearing a face protector. Hydrogen peroxide (33%) and iron (III) chloride were added at a 50:1 weight ratio (in Moles, the ratio was 10:1). First the iron (III) chloride was added, and then the hydrogen peroxide, which was added dropwise due to the reaction being exothermic, and producing a gas.

Stage 2 was performed in duplicate: one flask was stirred at room temperature for 72 hours, the other was stirred on the rotavapour (at atmospheric pressure) at 65° C. for 72 hours. At 24 hour intervals, the flasks would be stopped for one hour to allow settling, then 1 ml of the top layer was removed and placed into a vial for GC analysis.

GC Analysis

Samples were analysed on an Agilent 6890N Network GC System, with a 5973 Network Mass selective Detector.

Column was a 190915-433/HP-5MS, 0.25 mm×30 m×0.25 um. capillary, with helium as the mobile phase.

Method was adapted from an Agilent method for separation of triglycerides:

Start temp: 50° C.
Final temp: 350° C.
Ramp: 15° C. per min
Time at Start: 1 min
Time at Final: 0 mins
Injection volume was 1 μl.
Saved on GC as oil4

Flash Point Analysis

Performed using a Seta-Point series 3 closed cup device.

Viscosity Analysis

Performed with a Brookfield DV-E Viscometer at room temperature (20° C.), at 100 rpm.

Results

The results of this experiment are shown in the Table 1 of FIGS. 5A and 5B, and Tables 2 and 3 shown below.

TABLE 2

Viscosity measurements of samples.

| Sample | Viscosity (cPs) |
|---|---|
| Standard | 12 |
| Sample 1 | 64 |
| Sample 2 | 10 |

TABLE 3

Flash points of samples.

| Sample | Flash Point (CC) C. |
|---|---|
| Sample 1 | 158 |
| Methanol | 65 |
| Sample 2 | 175 |
| Sample 7 | 150 |
| Sample 6 | 160.5 |

Key for Tables 1, 2 & 3:
Sample 1: untreated vegetable oil
Sample 2: top layer, stage 1
Sample 3: Stage 1, 65 C, after 24 hours
Sample 4: Stage 1, room temperature, after 24 hours
Sample 5: Stage 1, 65 C, after 48 hours
Sample 6: Stage 1, room temperature, after 48 hours Sample 7: Stage 1, 100° C. after 48 hours Discussion & Conclusion Stage 1:

Our method produced, from 561 ml vegetable oil, 524 mls of methyl esters after Stage 1 treatment. This is a yield of 93.4%. The viscosity had been reduced by a factor of approximately 6, following stage 1 treatment.

The flash point of Stage 1 product was 12° C. higher than that of untreated vegetable oil. There were some indications from the literature that biodiesel has a higher flash point that other hydrocarbons.

It can be seen from the GC that after stage 1, the top layer appears to be totally made up of methyl esters (with the exception of a few trace compounds). 96.5% of the esters are the C18 oleic acid isomers, and almost all of these are the (z) form: 9-octadecenoic acid (z)-methyl ester. About 6% is the 11-isomer. TOP layer sample 2 was used for next stage.

Stage 2:

It is apparent that the flash point of sample was reduced by 25° C. after Fenton reaction followed by heating at 100 C. Where the sample mixed at room temperature only reduces flash point by 15° C.

From GCMS analysis, it can be seen that after 24 hours at 65 C, still the largest compound by far (78.17%) is 9-octadecenoic acid (z)-methyl ester, but in addition there was now 13% of the 8-isomer, which was not present in Stage 1. After 24 hours at room temperature, the largest compound (84.59%) was still 9-octadecenoic acid (z)-methyl ester. A new compound, 9,12,15-octadecatrien-1-ol, was the second largest (12.44%).

After 48 hours the largest amount is still 9-octadecenoic acid (z)-methyl ester (77.07%). As after 24 hours, the second largest peak is the 8-isomer.

Quantities Required

Amounts of each component used to produce a liter of the C18 C8 mix 1050 mls vegetable oil 144 mls of a 1.048M NaOH/MeOH solution 46 mls hydrogen peroxide 33%

2 g $Fe^{III}$

EXAMPLE 3

This example describes the optimisation pH of the cell suspension culture of oil-producing cells.

Method:

The original culture as described in section 6.2 of Example 1 was thoroughly agitated for ten minutes to achieve an even cell suspension, then aliquots were taken.

Aliquots of the main oil producing cell culture were buffered to various pH values as indicated in table 4, below, and the amount of oil produced per 100 ml aliquot, based on the oil that that collected on the surface of the cell culture medium that could be drawn off with a pipette, was measured in a measuring cylinder over a 14 day period.

The pH buffering was achieved with citric acid and disodium hydrogen orthophosphate according to the European Pharmacopoeia method.

Figure 6:
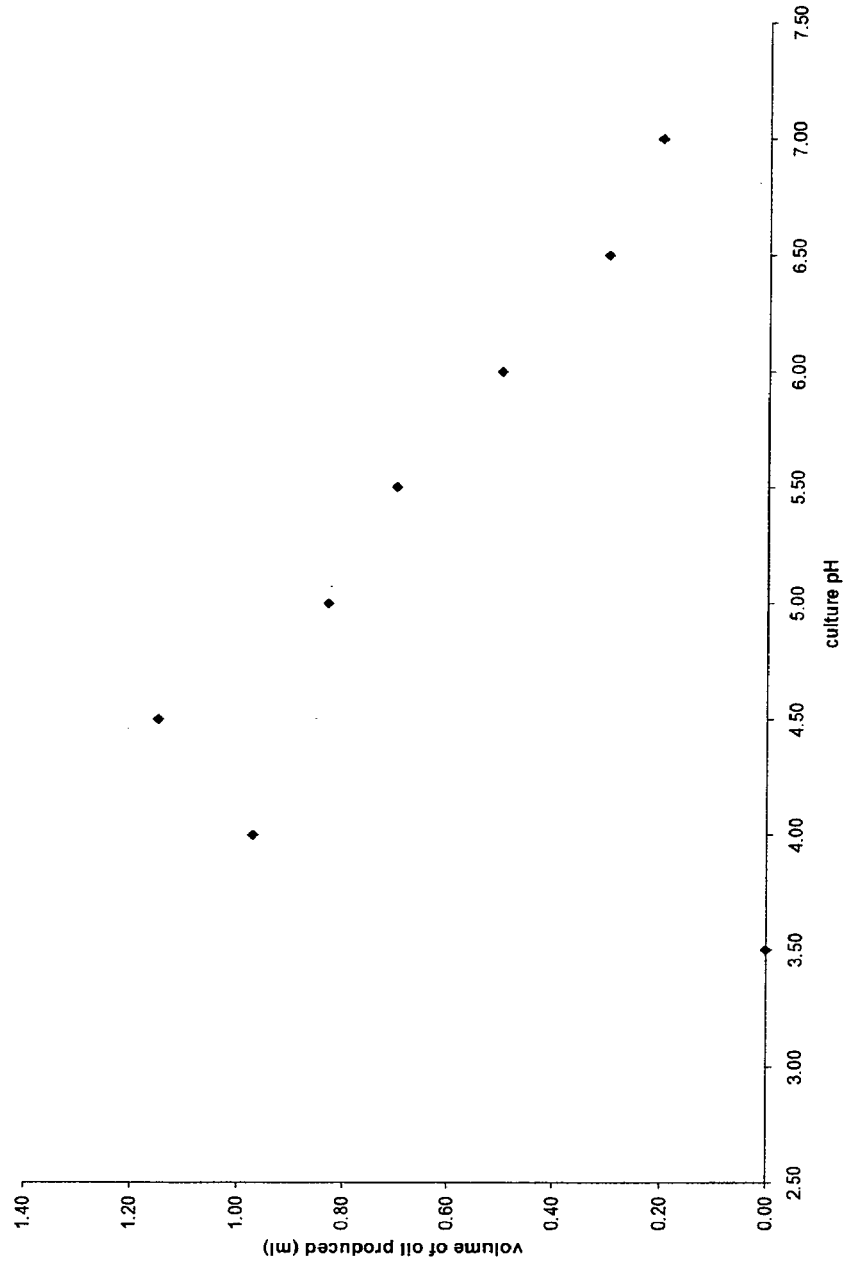
FIG. 6 shows the relationship between culture pH and the level of fatty acids and oils secreted and collected from a biphasic system, as described in Example 3.

Results:

The results of this experiment are shown in Table 4 and FIG. 6.

TABLE 4

| | pH | | | | | | | |
|---|---|---|---|---|---|---|---|---|
| | 7.00 | 6.50 | 6.00 | 5.50 | 5.00 | 4.50 | 4.00 | 3.50 |
| volume of oil produced (ml) | 0.20 | 0.30 | 0.50 | 0.70 | 0.83 | 1.15 | 0.97 | 0* |

*(cell death ensued at pH 3.5)

Discussion & Conclusion

The data shows that more oil is released at the optimum pH of 4.5 and that below this pH the optimum is not obtained due to acidic toxicity to the medium and associated cell death. Above the pH 4.5 level the optimum separation has not been achieved due to the formation of the emulsion not being as efficient.

EXAMPLE 4

This example describes the effect of the addition of lipase to the production of fatty acids in tissue culture.

Figure 8:
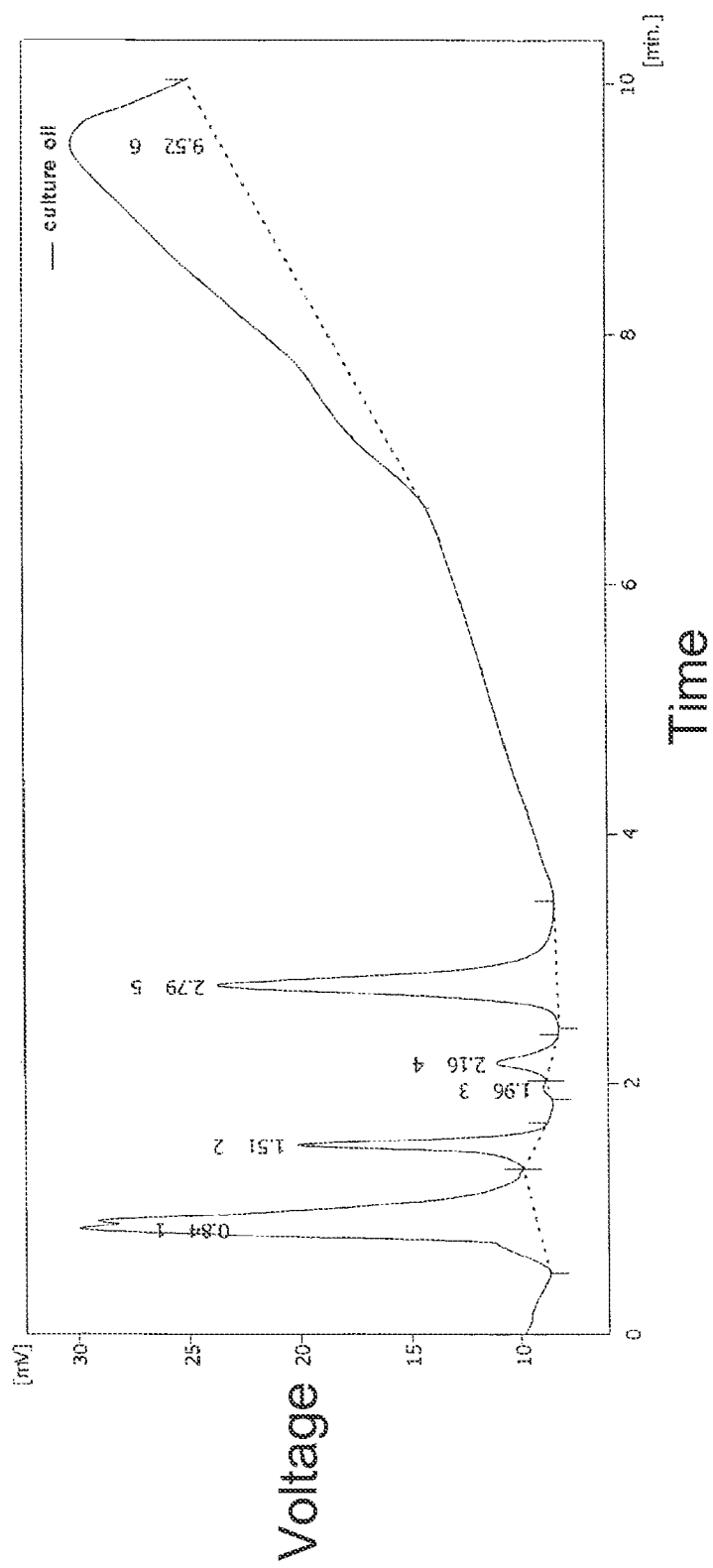
FIG. 8 shows gas chromatography analysis of the distribution of oils and non-glycerated fatty acids in an extract taken from the suspension culture as described in section 6.2 of Example 1.

Analysed by gas chromatography of the distribution of oils and non-glycerated fatty acids in an extract taken from a 'normal' cell suspension, i.e. the suspension culture as described in section 6.2 of Example 1, is shown in FIG. 8.

Lipase from wheat germ was purchased from Sigma Aldrich. 1 g of the lipase was added to 100 ml of the suspension culture as described in section 6.2 of Example 1. The resulting oil, as collected from the top layer of the culture using a pipette and analysed by gas chromatography, showed a breakdown with 8% of the oil being non-glycerated fatty acids when compared to the normal cell suspension product.

EXAMPLE 5

This example describes the use of a two-cell culture system according to the second aspect of the present invention.

Murashige and Skoog basal media was prepared and alpha napthalenic acid added at a concentration of 0.01M. The medium was inoculated with chloroplast containing cells from *Agrostis tenuis* and incubated as a cell suspension culture for 28 days in the presence of light and at 22° C.

After the twenty eight day incubation period the media was drawn off and the increase in sugar concentration was measured using refractometry. The concentration of the sugar ion the media was found to be above 50 g/l. This media was then incubated with oil producing cells from oil seed rape and incubated for another twenty eight days after which period an oil layer had formed above the layer of the media.

To scale this process up to industrial levels, for example, grow the cell suspension culture of chloroplast-containing (i.e. photosynthetic) cells in the culture medium using an air stream of about 3660 liters per minute for a 20,000 liter tank at a $CO_2$ density of about 10% with an absorption efficiency of about 40%. At a smaller scale, for example using 3 liters of culture, one could pass 0.55 liters per minute of a 10% $CO_2$/air mixture across this to have the same relative throughput.

The better the $CO_2$ absorption rate in the photosynthetic culture, the more efficient the process. The efficiency of $CO_2$ absorption will directly correlate with two factors—
1. The size of the bubble: the smaller the bubble the more efficient it will be, ideally the bubbles will have a mean average diameter at the point of introduction into the culture medium of about less than 1 mm, such as less than 0.5 mm, 0.4 mm, 0.3 mm, 0.2 mm. 0.1 mm, 90 mm, 80 mm, 70 mm, 60 mm, 50 mm, 40 mm, 30 mm, 20 mm, or 10 µm.
2. The length of time the bubble is in the culture: the taller the culture column the more time it takes the bubble to transit the medium and hence spends longer in the media. Typically, the column height is up to about 0.5 meter, 1 meter, 2 meters, 3 meters, 4 meters or 5 meters in height (in this context the term about is used to refer to ±05, 0.4, 0.3, 0.2 or 0.1 meters).

The $CO_2$ absorption rate can be assessed by comparing the $CO_2$ content (density) of the gas introduced into the culture with the $CO_2$ content (density) of the exhaust stream.

Since the introduction of gases into a cell suspension culture can cause adiabatic expansion cooling, it may be suitable to adjust the temperature of the gas feed (for example, by passing the feed tube through a heated water bath), or allow for gaseous expansion, prior to its introduction into the culture, to minimise or reduce the impact on culture temperature.

EXAMPLE 6

The following example describes apparatus for use in a two-cell culture system according to the second aspect of the present invention.

The model is based on two tanks of photosynthetic plant cell suspension cultures per tank of oil-producing plant cell suspension culture. With a large enough number of multiple tanks of each culture type (e.g. in a full scale production facility) this may be balanced out to the equivalent of about 1.6 tanks of photosynthetic plant cell suspension cultures per tank of plant oil-producing cell suspension culture.

The tank sizes each contain about 20,000 liters of media.

The tank of oil-producing plant cell suspension culture produces fatty acids and oils at a rate of 10% (volume) every 10 days, i.e. 1% per day, or 200 liters per day.

Each liter of oil requires about 1.6 kg of sucrose (1,600 grams) or equivalent sugar.

The photosynthetic plant cell suspension culture can be grown to produce, and maintained at, a culture medium concentration of 50 grams of sucrose per liter of culture. The sugar is typically about 58% by mass water so 29 ml of water needs to be replenished every day per liter of photosynthetic plant cell suspension culture media.

Figure 7:
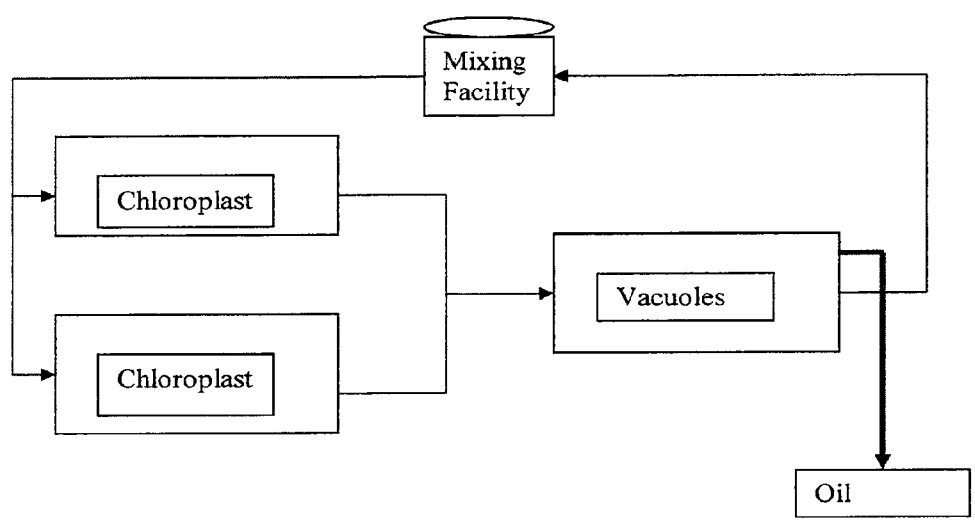
FIG. 7 shows an exemplary apparatus for use in a two-cell culture system as described in Example 6, wherein the term "chloroplast" is used to refer to a tank of photosynthetic plant cell suspension culture and the term "vacuole" is used to refer to a tank of oil-producing plant cell suspension culture.

The setup of an exemplary apparatus for use in this method is shown in FIG. 7, wherein the term "chloroplast" is used to refer to a tank of photosynthetic plant cell suspension culture and the term "vacuole" is used to refer to a tank of oil-producing plant cell suspension culture.

On a daily basis, the set up illustrated in FIG. 7 can be run as follows:
1. Pump 6400 liters of filtered media from the Vacuole tank to the mixing facility
2. Add 600 liters of purified water of plus the constituents for 600 liters of media (60,000*1/100) into the mixing vessels and mix (60,000 liters of media being the total media volume)
3. Pump 3500 liters of this mixture into each chloroplast vessel. This replaces the amount of water used up by the chloroplast in a 24 hour timeframe. The chloroplast media should now be at the right concentration for replacing the media taken out of the vacuole tank.
4. Pump 3200 liters from each chloroplast tank into the vacuole tank.

This will be operated on a 24 hour cycle. However, if a pulse system was used every hour, which should improve the stability of cultures, then each pulse would be $\frac{1}{24}^{th}$ of the above, i.e. the above daily process of steps 1-4 could be operated more regularly, such as every hour, and the volumes scaled down accordingly.

Further Disclosure:

The present invention also provides a method for producing vegetable oils from tissue culture cell lines derived from plants. The vegetable oils produced may be used to manufacture bio-fuels. Enzymes may be used in this method to inhibit the glyceration of fatty acids. The cells produced during the tissue culture stage of this method may be fermented to produce ethanol, and optionally the ethanol may be used as fuel source. The vegetable oils produced by the method may be of a form that is identical to that produced by the source plant through conventional methods.

The invention claimed is:

1. A method for the production of a biological product, the method comprising:
   (i) culturing a first cell suspension culture of non-algal photosynthetic plant cells in a culture medium under conditions to photosynthesize, generate and secrete sugars into the culture medium; and
   (ii) culturing a second cell culture of cells in a culture medium comprising the sugars generated by the first cell suspension culture to grow the second cell culture and produce a biological product, wherein the second cell culture is cultured in the presence of the sugars generated by the first cell suspension culture at a sugar concentration in the range of 20 g/L to 400 g/L.

2. The method of claim 1, wherein the biological product is the cells of the second cell culture.

3. The method of claim 1, wherein the biological product is synthesized by the cells of the second cell culture.

4. The method of claim 1, wherein the non-algal photosynthetic cells of the first cell suspension culture and the cells of the second cell culture are in fluid communication with each other.

5. The method of claim 4, wherein the non-algal photosynthetic cells of the first cell suspension culture and the cells of the second cell culture are mixed together and cultured in the same medium.

6. The method of claim 4, wherein the non-algal photosynthetic cells of the first cell suspension culture and the cells of the second suspension culture are cultured in separated culture vessels that are in fluid communication with each other.

7. The method of claim 4, wherein the fluid communication between the non-algal photosynthetic cells of the first cell suspension culture and the cells of the second cell culture allows the sugar secreted by the non-algal photosynthetic cells of the first cell suspension culture to be used as a carbon source by the cells of the second cell culture.

8. The method of claim 1, wherein the non-algal photosynthetic cells of the first cell suspension culture and the cells of the second cell culture are each grown in separate culture vessels that are not in fluid communication with each other.

9. The method of claim 8, further comprising a step of extracting the sugars from the culture medium of the first cell suspension culture and a further step of feeding the extracted sugars into the second cell culture.

10. The method of claim 9, wherein the step of extracting the sugars from the culture medium of the first cell suspension culture comprises separating a sugar-containing medium of the first cell culture from the non-algal photosynthetic cells present therein.

11. The method of claim 9, wherein the step of extracting sugars from the culture medium of the first cell suspension culture comprises continuously removing sugars from the cell culture medium of the first cell suspension culture.

12. The method of claim 1, wherein the second cell culture is cultured in the presence of sugars generated by the first cell suspension culture at a sugar concentration selected from the group consisting of up to 300 g/L, up to 200 g/L, up to 100 g/L or 50 g/L.

13. The method of claim 3, wherein the biological product is selected from the group consisting of at least one fatty acid and/or oil, a proteinaceous product and a metabolite.

14. The method of claim 1, wherein the cells of the second cell culture are selected from the group consisting of prokaryotic cells, eukaryotic cells, bacterial cells, fungal cells, plant cells, animal cells and human cells.

15. The method of claim 1, wherein the cells of the second cell culture are microorganisms and optionally the biological product is an alcohol.

16. The method of claim 1, wherein the method is a method for the production of at least one fatty acid and/or oil from a plant cell culture, wherein step (ii) is a method comprising culturing a second cell suspension culture of oil-producing plant cells in a culture medium comprising the sugars generated by the first cell suspension culture and under conditions to produce at least one fatty acid and/or oil.

17. The method of claim 1, further comprising a step of extracting the biological product from the second cell culture.

18. The method of claim 16, further comprising a step of extracting the at least one fatty acid and/or oil from the second cell suspension culture of oil-producing plant cells.

19. The method of claim 17, further comprising purifying and/or processing the extracted biological product.

20. The method of claim 18, further comprising purifying and/or processing the extracted at least one fatty acid and/or oil.

21. The method of claim 18, comprising:
(i) maintaining the second cell suspension culture of oil-producing plant cells under conditions to synthesise and secrete at least one fatty acid and/or oil into the culture medium; and
(ii) extracting the secreted fatty acid and/or oil from the culture medium.

22. The method of claim 21, wherein the fatty acid and/or oil that is extracted is further processed and converted to a biofuel, or is optionally further purified and/or used in a downstream process.

23. The method of claim 1, wherein the non-algal photosynthetic plant cells in the first cell suspension culture are differentiated non-algal photosynthetic plant cells.

24. The method of claim 23, wherein the differentiated non-algal photosynthetic plant cells are cells specialized for photosynthesis.

25. The method of claim 24, wherein the differentiated non-algal photosynthetic plant cells in the first cell suspension culture are palisade cells.

26. The method of claim 1, wherein the non-algal photosynthetic plant cells in the first cell suspension culture are isolated from a copper-tolerant plant.

27. The method of claim 26, wherein the first cell suspension culture of non-algal photosynthetic plant cells has a cell culture medium copper level of up to 0.1 M.

28. The method of claim 16, wherein the oil-producing plant cell in the second cell suspension culture is a differentiated oil-producing plant cell.

29. The method of claim 28, wherein the differentiated oil-producing plant cell is a mesoderm cell.

30. The method of claim 1, wherein the first cell suspension culture of non algal photosynthetic plant cells is fed carbon dioxide from a carbon dioxide source selected from the group consisting of liquid carbon dioxide and gaseous carbon dioxide.

31. The method of claim 30, wherein the carbon dioxide source is obtained as a by-product of a carbon dioxide-producing process.

32. The method of claim 31, wherein at least the first cell suspension culture, and optionally also the second cell culture, is or are maintained at the site of the carbon dioxide-producing process.

* * * * *